US012697325B2

(12) United States Patent
Ma et al.

(10) Patent No.: US 12,697,325 B2
(45) Date of Patent: Aug. 4, 2026

(54) PHARMACEUTICAL COMPOSITION COMPRISING SULBACTAM AND AVIBACTAM, AND APPLICATION THEREOF

(71) Applicant: TENNOR THERAPEUTICS (SUZHOU) LIMITED, Suzhou (CN)

(72) Inventors: Zhenkun Ma, Suzhou (CN); Yue Xu, Suzhou (CN); Yu Liu, Suzhou (CN); Huan Wang, Suzhou (CN); Shijie He, Suzhou (CN); Yan Zhang, Suzhou (CN); Xiangyi Xu, Suzhou (CN)

(73) Assignee: TENNOR THERAPEUTICS (SUZHOU) LIMITED, Suzhou (CN)

(*) Notice: Subject to any disclaimer, the term of this patent is extended or adjusted under 35 U.S.C. 154(b) by 382 days.

(21) Appl. No.: 18/243,768

(22) Filed: Sep. 8, 2023

(65) Prior Publication Data

US 2024/0000755 A1 Jan. 4, 2024

Related U.S. Application Data

(63) Continuation of application No. PCT/CN2022/114979, filed on Aug. 26, 2022.

(30) Foreign Application Priority Data

Aug. 27, 2021 (CN) ......................... 202110996492.4

(51) Int. Cl.
*A61K 31/43* (2006.01)
*A61K 31/4188* (2006.01)
(Continued)

(52) U.S. Cl.
CPC .......... *A61K 31/43* (2013.01); *A61K 31/4188* (2013.01); *A61K 31/65* (2013.01); *A61K 38/12* (2013.01); *A61P 31/04* (2018.01)

(58) Field of Classification Search
CPC .. A61K 31/4188; A61K 31/43; A61K 31/546; A61K 31/65; A61K 38/12;
(Continued)

(56) References Cited

U.S. PATENT DOCUMENTS

| | | | | |
|---|---|---|---|---|
| 2014/0094447 A1* | 4/2014 | Bhagwat | ................ | A61K 31/43<br>514/210.05 |
| 2019/0022102 A1* | 1/2019 | Gordon | ................ | A61K 31/551 |

FOREIGN PATENT DOCUMENTS

| | | |
|---|---|---|
| CN | 103648496 A | 3/2014 |
| CN | 103687598 A | 3/2014 |
| CN | 113559099 A | 10/2021 |

OTHER PUBLICATIONS

Haginaka et al., Degradation Kinetics of Sodium Sulbactam in Aqueous Solutions, Chemical and Pharmaceutical Bulletin, vol. 33, No. 6, 2461-2468, 1985 (Year: 1985).*

(Continued)

*Primary Examiner* — Sarah Pihonak
*Assistant Examiner* — Padmaja S Rao
(74) *Attorney, Agent, or Firm* — Merchant & Gould P.C.; Daniel J. Pereira

(57) ABSTRACT

The present application relates to a pharmaceutical composition comprising sulbactam or a pharmaceutically acceptable salt thereof, avibactam or a pharmaceutically acceptable salt thereof, and optionally a pharmaceutically acceptable carrier, wherein unit dose ratio of said sulbactam or the pharmaceutically acceptable salt thereof and said avibactam or the pharmaceutically acceptable salt thereof is about 8:1 to about 4:1, unit dose of said sulbactam or the pharmaceutically acceptable salt thereof is about 1 g-4 g, and unit dose of said avibactam or the pharmaceutically acceptable salt thereof is about 0.125 g-1 g. The present
(Continued)

application also relates to methods of treating bacterial infections using said pharmaceutical composition.

18 Claims, 1 Drawing Sheet

(51) Int. Cl.

| | |
|---|---|
| ***A61K 31/65*** | (2006.01) |
| ***A61K 38/12*** | (2006.01) |
| ***A61P 31/04*** | (2006.01) |

(58) Field of Classification Search
CPC .... A61K 31/439; A61K 45/06; A61K 9/0019; A61P 31/04
See application file for complete search history.

(56) References Cited

OTHER PUBLICATIONS

PCT/CN2022/114979 International Search Report dated Nov. 3, 2022.
Pasteran, F. et al., A New Twist: The Combination of Sulbactam/Avibactam Enhances Sulbactam Activity Against Carbapenem-Resistant *Acinetobacter baumannii*(CRAB) Isolates, Antibiotics, vol. 10, No. 577, MDPI, May 13, 2021.
Rodriguez, C.H., et al., In Vitro Synergistic Activity of the Sulbactam/Avibactam Combination Against Extensively Drug-Resistant Aceinetobacter baumannii, J of Medical Microbiology, vol. 69, pp. 928-931, The Authors, Jun. 25, 2020.

* cited by examiner

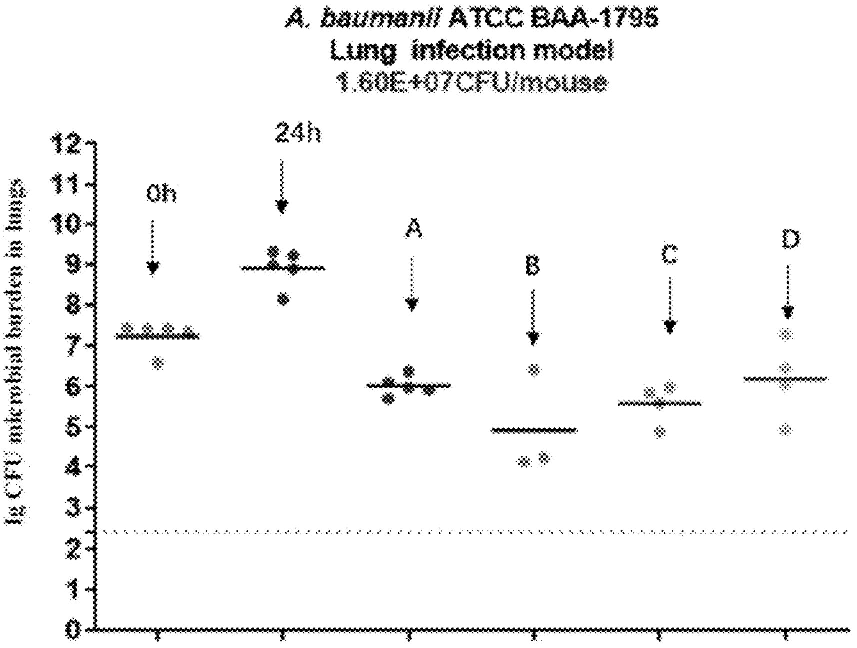
- 0 h Control
- 24 h Control
- A: Tigecycline, 300 mg/kg, i.p., b.i.d.
- B: Sulbactam/avibactam: 300 mg/75 mg/kg
- C: Sulbactam/avibactam: 150 mg/37.5 mg/kg
- D: Sulbactam/avibactam: 75 mg/18.75 mg/kg
(B–D) 3h, intravenous infusion, 150 μL/h, q6h

PHARMACEUTICAL COMPOSITION COMPRISING SULBACTAM AND AVIBACTAM, AND APPLICATION THEREOF

CROSS-REFERENCE TO RELATED APPLICATIONS

This application is a Continuation of and claims priority under 35 U.S.C. § 111 to Patent Cooperation Treaty application PCT/CN2022/114979, filed Aug. 26, 2022, which claims the benefit of Chinese Patent Application No. 202110996492.4, filed Aug. 27, 2021. Priority is claimed to both of these applications and the disclosures of these prior applications are considered part of the disclosure of this application and to the extent allowed the entire contents of the aforementioned applications are incorporated herein.

FIELD OF THE INVENTION

The present application relates to the field of biomedicine, particularly to a pharmaceutical composition comprising avibactam and sulbactam, and its application in the treatment of bacterial infections.

BACKGROUND OF THE INVENTION

Bacterial infections (such as *Acinetobacter baumannii*) may cause nosocomial pneumonia, bloodstream infection, intra-abdominal infection, central nervous system infection, urinary system infection, skin and soft tissue infection, etc., and due to the bacterial isolation rate, infection rate and drug resistance are increasing year by year. This problem has become a global challenge in the field of anti-infection.

Due to the serious problem of drug resistance, there are limited options for safe and effective drugs available for the treatment of drug-resistant bacterial infections. For example, the drugs currently used for the treatment of drug-resistant *Acinetobacter baumannii* include polymyxin, tigecycline, and a few other drugs, such as sulbactam and compound formulations of sulbactam-containing β-lactamase inhibitors and β-lactam antibiotics. However, there are problems such as insufficient experience in clinical use and high incidences of adverse reactions. Moreover, the sharp rise of bacterial drug resistance makes the existing clinical therapies have increasingly lower clinical efficacy for patients with bacterial infections (Chinese Expert Consensus on Diagnosis, Treatment and Prevention of *Acinetobacter baumannii* Infection, Chinese Medical Journal, 2012, 92, 76-85.).

Bacterial infections have long been associated with high mortality rates and are becoming more lethal with the increase in bacterial drug resistance. Therefore, there is an urgent need to develop new methods to treat bacterial infections, especially drug-resistant bacterial infections.

SUMMARY OF THE INVENTION

The present application provides a pharmaceutical composition, and said pharmaceutical composition comprises sulbactam or a pharmaceutically acceptable salt thereof and avibactam or a pharmaceutically acceptable salt thereof, and optionally a pharmaceutically acceptable carrier, wherein unit dose ratio (mass ratio) of said sulbactam or the pharmaceutically acceptable salt thereof and said avibactam or the pharmaceutically acceptable salt thereof is about 8:1 to about 4:1, unit dose of said sulbactam or the pharmaceutically acceptable salt thereof is about 1 g-4 g, and unit dose of said avibactam or the pharmaceutically acceptable salt thereof is about 0.125 g-1 g. The inventors of the present application surprisingly found that sulbactam or its pharmaceutically acceptable salt or avibactam or its pharmaceutically acceptable salt administered as monotherapy in a specific ratio can effectively increase the bacteriostatic concentration achieved by the combination use of sulbactam or its pharmaceutically acceptable salt and avibactam or its pharmaceutically acceptable salt, exerting a favorable bacteriostatic effect.

In one aspect, the present application provides a pharmaceutical composition, and said pharmaceutical composition comprises sulbactam or a pharmaceutically acceptable salt thereof and avibactam or a pharmaceutically acceptable salt thereof, and optionally a pharmaceutically acceptable carrier, wherein unit dose ratio (mass ratio) of said sulbactam or the pharmaceutically acceptable salt thereof and said avibactam or the pharmaceutically acceptable salt thereof is about 8:1 to about 4:1, unit dose of said sulbactam or the pharmaceutically acceptable salt thereof is about 1 g-4 g, and unit dose of said avibactam or the pharmaceutically acceptable salt thereof is about 0.125 g-1 g.

In some embodiments, the unit dose ratio of said sulbactam or the pharmaceutically acceptable salt thereof and said avibactam or the pharmaceutically acceptable salt thereof is about 4:1 in said pharmaceutical composition.

In some embodiments, the unit dose of said sulbactam or the pharmaceutically acceptable salt thereof in said pharmaceutical composition is about 1 g-3 g.

In some embodiments, the unit dose of said sulbactam or the pharmaceutically acceptable salt thereof is about 2 g in said pharmaceutical composition.

In some embodiments, the unit dose of said avibactam or the pharmaceutically acceptable salt thereof is about 0.25 g-1 g in said pharmaceutical composition.

In some embodiments, the unit dose of said avibactam or the pharmaceutically acceptable salt thereof is about 1 g in said pharmaceutical composition.

In some embodiments, the unit dose of said avibactam or the pharmaceutically acceptable salt thereof is about 0.5 g in said pharmaceutical composition.

In some embodiments, in said pharmaceutical composition, said sulbactam or the pharmaceutically acceptable salt thereof comprises sulbactam sodium and/or sulbactam calcium.

In some embodiments, in said pharmaceutical composition, said sulbactam or the pharmaceutically acceptable salt thereof is sulbactam sodium.

In some embodiments, in said pharmaceutical composition, said avibactam or the pharmaceutically acceptable salt thereof comprises avibactam sodium and/or avibactam calcium.

In some embodiments, in said pharmaceutical composition, said avibactam or the pharmaceutically acceptable salt thereof is avibactam sodium.

In some embodiments, said pharmaceutical composition is prepared to be suitable for administration via injection.

In some embodiments, said pharmaceutical composition is prepared to be suitable for intravenous injection.

In some embodiments, said pharmaceutical composition is prepared as a solid or liquid.

In some embodiments, said pharmaceutical composition is prepared as an injection.

In some embodiments, the pH of said pharmaceutical composition is about 4 to about 8.

In some embodiments, the pH of said pharmaceutical composition is about 5 to about 7.3.

In some embodiments, the pH of said pharmaceutical composition is about 5 to about 6.

In some embodiments, in said pharmaceutical composition, said sulbactam or the pharmaceutically acceptable salt thereof and said avibactam or the pharmaceutically acceptable salt thereof are present in the same container.

In some embodiments, in said pharmaceutical composition, said sulbactam or the pharmaceutically acceptable salt thereof and said avibactam or the pharmaceutically acceptable salt thereof are each independently present in different containers.

In another aspect, the present application provides a kit or an administration device, said kit or administration device comprises the pharmaceutical composition of the present application.

In another aspect, the present application provides the use of said pharmaceutical composition of the present application in the manufacture of a medicament; and said medicament is for the prevention, treatment and/or alleviation of bacterial infections.

In another aspect, the present application provides the use of sulbactam or a pharmaceutically acceptable salt thereof and avibactam or a pharmaceutically acceptable salt thereof in the manufacture of a medicament, wherein ratio of administration dosage of said sulbactam or the pharmaceutically acceptable salt thereof to said avibactam or the pharmaceutically acceptable salt thereof is about 8:1 to about 4:1; administration dosage of said sulbactam or the pharmaceutically acceptable salt thereof is about 4 g-12 g/day and administration dosage of said avibactam or the pharmaceutically acceptable salt thereof is about 0.5 g-3 g/day.

In some embodiments, the administration dosage ratio of said sulbactam or the pharmaceutically acceptable salt thereof and said avibactam or the pharmaceutically acceptable salt thereof is about 4:1.

In some embodiments, the administration dosage of said sulbactam or the pharmaceutically acceptable salt thereof is about 4 g-8 g/day.

In some embodiments, dosing interval of said sulbactam or the pharmaceutically acceptable salt thereof is every 6 hours-8 hours.

In some embodiments, dosing frequency of said sulbactam or the pharmaceutically acceptable salt thereof is 2 times-4 times daily.

In some embodiments, the administration dosage of said sulbactam or the pharmaceutically acceptable salt thereof is about 1 g-3 g each time.

In some embodiments, the administration dosage of said sulbactam or the pharmaceutically acceptable salt thereof is about 2 g each time.

In some embodiments, the administration dosage of said sulbactam or the pharmaceutically acceptable salt thereof is about 8 g/day.

In some embodiments, the dosing interval of said sulbactam or the pharmaceutically acceptable salt thereof is every 6 hours.

In some embodiments, the dosing frequency of said sulbactam or the pharmaceutically acceptable salt thereof is 4 times daily.

In some embodiments, the administration dosage of said sulbactam or the pharmaceutically acceptable salt thereof is about 6 g/day.

In some embodiments, the dosing interval of said sulbactam or the pharmaceutically acceptable salt thereof is every 8 hours.

In some embodiments, the dosing frequency of said sulbactam or the pharmaceutically acceptable salt thereof is 3 times daily.

In some embodiments, the administration dosage of said avibactam or the pharmaceutically acceptable salt thereof is about 1 g-2 g/day.

In some embodiments, dosing interval of said avibactam or the pharmaceutically acceptable salt thereof is every 6 hours-8 hours.

In some embodiments, dosing frequency of said avibactam or the pharmaceutically acceptable salt thereof is 2 times-4 times daily.

In some embodiments, the administration dosage of said avibactam or the pharmaceutically acceptable salt thereof is 0.25 g-1 g each time.

In some embodiments, the administration dosage of said avibactam or the pharmaceutically acceptable salt thereof is 0.5 g each time.

In some embodiments, the administration dosage of said avibactam or the pharmaceutically acceptable salt thereof is about 2 g/day.

In some embodiments, the dosing interval of said avibactam or the pharmaceutically acceptable salt thereof is every 6 hours.

In some embodiments, the dosing frequency of said avibactam or the pharmaceutically acceptable salt thereof is 4 times daily.

In some embodiments, the administration dosage of said avibactam or the pharmaceutically acceptable salt thereof is about 1.5 g/day.

In some embodiments, the dosing interval of said avibactam or the pharmaceutically acceptable salt thereof is every 8 hours.

In some embodiments, the dosing frequency of said avibactam or the pharmaceutically acceptable salt thereof is 3 times daily.

In some embodiments, said sulbactam or the pharmaceutically acceptable salt thereof comprises sulbactam sodium and/or sulbactam calcium.

In some embodiments, said sulbactam or the pharmaceutically acceptable salt thereof is sulbactam sodium.

In some embodiments, said avibactam or the pharmaceutically acceptable salt thereof is avibactam sodium.

In some embodiments, said medicament is prepared to be suitable for administration via injection.

In some embodiments, said medicament is prepared to be suitable for intravenous injection.

In some embodiments, said medicament is prepared as a solid or liquid.

In some embodiments, said medicament is prepared as an injection.

In some embodiments, the pH of said medicament is about 4 to about 8.

In some embodiments, the pH of said medicament is about 5 to about 7.3.

In some embodiments, the pH of said medicament is about 5 to about 6.

In some embodiments, said sulbactam or the pharmaceutically acceptable salt thereof and said avibactam or the pharmaceutically acceptable salt thereof are present in the same container.

In some embodiments, said sulbactam or the pharmaceutically acceptable salt thereof and said avibactam or the pharmaceutically acceptable salt thereof are each independently present in different containers.

In some embodiments, said use comprises simultaneous administration of said sulbactam or the pharmaceutically acceptable salt thereof and said avibactam or the pharmaceutically acceptable salt thereof.

In some embodiments, injection duration of said medicament lasts 2 hours-4 hours.

In some embodiments, said bacteria comprise a bacterium that produces one or more β-lactamases.

In some embodiments, said bacteria comprise a bacterium that produces one or more type A β-lactamases.

In some embodiments, said bacteria comprise a bacterium that produces one or more type B β-lactamases.

In some embodiments, said bacteria comprise a bacterium that produces one or more type C β-lactamases.

In some embodiments, said bacteria comprise a bacterium that produces one or more type D β-lactamases.

In some embodiments, said bacteria are resistant to one or more antibiotics.

In some embodiments, said bacteria are resistant to one or more β-lactam antibiotics.

In some embodiments, said bacteria are resistant to cephalosporins, carbapenems, fluoroquinolones, and/or aminoglycosides.

In some embodiments, said bacteria are resistant to one or more antibiotics selected from the group consisting of cefoperazone, sulbactam, amikacin, levofloxacin and minocycline.

In some embodiments, said bacteria comprise *Acinetobacter baumannii.*

In some embodiments, said bacterial infections are respiratory tract infection, bloodstream infection, intra-abdominal infection, skin and soft tissue infection, urinary system infection or central nervous system infection.

In some embodiments, said bacterial infection is a lung infection.

In some embodiments, said bacterial infection is pneumonia.

In some embodiments, said medicament is used in combination with one or more other antibacterial agents.

In some embodiments, said medicament is used in combination with polymyxin.

In some embodiments, said medicament is used in combination with tigecycline.

In another aspect, the present application provides a method for preventing, treating and/or alleviating bacterial infections and said method comprises administering to a patient in need thereof the pharmaceutical composition of the present application.

In another aspect, the present application provides a method for preventing, treating and/or alleviating bacterial infections, wherein said method comprises administering to a patient in need thereof sulbactam or a pharmaceutically acceptable salt thereof and avibactam or a pharmaceutically acceptable salt thereof, wherein ratio of administration dosage of said sulbactam or the pharmaceutically acceptable salt thereof to said avibactam or the pharmaceutically acceptable salt thereof is about 8:1 to about 4:1, administration dosage of said sulbactam or the pharmaceutically acceptable salt thereof is about 4 g-12 g/day, and administration dosage of said avibactam or the pharmaceutically acceptable salt thereof is about 0.5 g-3 g/day.

In some embodiments, the administration dosage ratio of said sulbactam or the pharmaceutically acceptable salt thereof and said avibactam or the pharmaceutically acceptable salt thereof is about 4:1.

In some embodiments, the administration dosage of said sulbactam or the pharmaceutically acceptable salt thereof is about 4 g-8 g/day.

In some embodiments, dosing interval of said sulbactam or the pharmaceutically acceptable salt thereof is every 6 hours-8 hours.

In some embodiments, dosing frequency of said sulbactam or the pharmaceutically acceptable salt thereof is 2 times-4 times daily.

In some embodiments, the administration dosage of said sulbactam or the pharmaceutically acceptable salt thereof is 2 g each time.

In some embodiments, the administration dosage of said sulbactam or the pharmaceutically acceptable salt thereof is about 8 g/day.

In some embodiments, the dosing interval of said sulbactam or the pharmaceutically acceptable salt thereof is every 6 hours.

In some embodiments, the dosing frequency of said sulbactam or the pharmaceutically acceptable salt thereof is 4 times daily.

In some embodiments, the administration dosage of said sulbactam or the pharmaceutically acceptable salt thereof is about 6 g/day.

In some embodiments, the dosing interval of said sulbactam or the pharmaceutically acceptable salt thereof is every 8 hours.

In some embodiments, the dosing frequency of said sulbactam or the pharmaceutically acceptable salt thereof is 3 times daily.

In some embodiments, the administration dosage of said avibactam or the pharmaceutically acceptable salt thereof is about 1 g-2 g/day.

In some embodiments, dosing interval of said avibactam or the pharmaceutically acceptable salt thereof is every 6 hours-8 hours.

In some embodiments, dosing frequency of said avibactam or the pharmaceutically acceptable salt thereof is 2 times-4 times daily.

In some embodiments, the administration dosage of said avibactam or the pharmaceutically acceptable salt thereof is about 0.25 g-1 g each time.

In some embodiments, the administration dosage of said avibactam or the pharmaceutically acceptable salt thereof is about 0.5 g each time.

In some embodiments, the administration dosage of said avibactam or the pharmaceutically acceptable salt thereof is about 2 g/day.

In some embodiments, the dosing interval of said avibactam or the pharmaceutically acceptable salt thereof is every 6 hours.

In some embodiments, the dosing frequency of said avibactam or the pharmaceutically acceptable salt thereof is 4 times daily.

In some embodiments, the administration dosage of said avibactam or the pharmaceutically acceptable salt thereof is about 1.5 g/day.

In some embodiments, the dosing interval of said avibactam or the pharmaceutically acceptable salt thereof is every 8 hours.

In some embodiments, the dosing frequency of said avibactam or the pharmaceutically acceptable salt thereof is 3 times daily.

In some embodiments, said sulbactam or the pharmaceutically acceptable salt thereof comprises sulbactam sodium and/or sulbactam calcium.

In some embodiments, said sulbactam or the pharmaceutically acceptable salt thereof is sulbactam sodium.

In some embodiments, said avibactam or the pharmaceutically acceptable salt thereof comprises avibactam sodium and/or avibactam calcium.

In some embodiments, said avibactam or the pharmaceutically acceptable salt thereof is avibactam sodium.

In some embodiments, said method comprises administration via injection.

In some embodiments, said method comprises intravenous injection.

In some embodiments, said sulbactam or the pharmaceutically acceptable salt thereof and said avibactam or the pharmaceutically acceptable salt thereof are present in the same container.

In some embodiments, said sulbactam or the pharmaceutically acceptable salt thereof and said avibactam or the pharmaceutically acceptable salt thereof are each independently present in different containers.

In some embodiments, said method comprises simultaneous administration of said sulbactam or the pharmaceutically acceptable salt thereof and said avibactam or the pharmaceutically acceptable salt thereof.

In some embodiments, injection duration lasts 2 hours-4 hours.

In some embodiments, said bacteria comprise a bacterium that produces one or more 3-lactamases.

In some embodiments, said bacteria comprise a bacterium that produces one or more type A β-lactamases.

In some embodiments, said bacteria comprise a bacterium that produces one or more type B β-lactamases.

In some embodiments, said bacteria comprise a bacterium that produces one or more type C β-lactamases.

In some embodiments, said bacteria comprise a bacterium that produces one or more type D β-lactamases.

In some embodiments, said bacteria are resistant to one or more antibiotics.

In some embodiments, said bacteria are resistant to one or more β-lactam antibiotics.

In some embodiments, said bacteria are resistant to cephalosporins, carbapenems, fluoroquinolones, and/or aminoglycosides.

In some embodiments, said bacteria are resistant to one or more antibiotics selected from the group consisting of cefoperazone, sulbactam, amikacin, levofloxacin and minocycline.

In some embodiments, said bacteria comprise *Acinetobacter baumannii.*

In some embodiments, said bacterial infections are respiratory tract infection, bloodstream infection, intra-abdominal infection, skin and soft tissue infection, urinary system infection or central nervous system infection.

In some embodiments, said bacterial infection is a lung infection.

In some embodiments, said bacterial infection is pneumonia.

In some embodiments, said method is used in combination with one or more other antibacterial agents.

In some embodiments, said method is used in combination with polymyxin.

In some embodiments, said method is used in combination with tigecycline.

Other aspects and advantages of the present application can be readily appreciated by those skilled in the art from the detailed description below. Only illustrative embodiments of the present application are shown and described in the detailed description below. As will be appreciated by those skilled in the art, the contents of the present application enable those skilled in the art to modify the disclosed embodiments without departing from the spirit and scope of the invention contemplated in the present application. Accordingly, the descriptions in the drawings and specifications of the present application are only to be regarded as illustrative in nature, and not as restrictive.

BRIEF DESCRIPTION OF THE DRAWING

Specific features of the present invention to which the present application relates are shown in the appended claims. The features and advantages of the present invention can be better understood with reference to the examples and drawings described in detail below. A brief description of the attached drawings is as follows:

The FIGURE shows the antibacterial effect of the pharmaceutical composition of the present application on a mouse model of pneumonia.

DETAILED DESCRIPTION

Embodiments of the present invention are described below using specific examples, and other advantages and effects of the present invention can be readily appreciated by those skilled in the art based on the contents disclosed in the present description.

DEFINITIONS OF TERMS

In the present application, the term "pharmaceutical composition" generally refers to a mixture containing one or more compounds or physiologically/pharmaceutically acceptable salts or prodrugs thereof. Said one or more compounds or physiologically/pharmaceutically acceptable salts or prodrugs thereof exist as active ingredients in the pharmaceutical compositions. The pharmaceutical composition may generally also comprise other components, which may be physiologically or pharmaceutically acceptable carriers and/or excipients. The pharmaceutical composition allows said active ingredient to be in an effective form and does not contain other components having unacceptable toxicity to the patients to whom the composition is to be administered.

In the present application, the term "sulbactam" generally refers to a β-lactamase inhibitor. The chemical name of sulbactam may be (2S, 5R)-3,3-dimethyl-7-oxo-4-thia-1-azabicyclo [3.2.0] heptane-2-carboxylic acid 4,4-dioxide and it has the following structure:

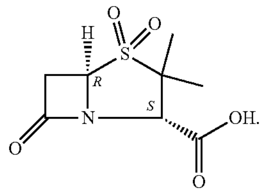

The chemical structure and physicochemical properties of sulbactam can be found under CAS No. 68373-14-8. The term "sulbactam" as used in the present application also includes commercially relevant formulations comprising (2S, 5R)-3, 3-dimethyl-7-oxo-4-thia-1-thiabicyclo [3.2.0]

heptane-2-carboxylic acid 4,4-dioxide sodium salt, such as the combination products containing sulbactam or a salt thereof and ampicillin or cefoperazone or a salt thereof. In the present application, sulbactam may form stable pharmaceutically acceptable acid or base salts, in which case it may be appropriate to administer the compound in the form of salt to patients. The term “sulbactam or a pharmaceutically acceptable salt thereof” used in the present application also includes any physical form thereof, such as crystalline or amorphous, stereoisomeric and optically active form. For example, commonly used pharmaceutically acceptable salts of sulbactam may include sulbactam sodium and/or sulbactam calcium.

In the present application, the term “sulbactam sodium” generally refers to a compound with the structural formula of:

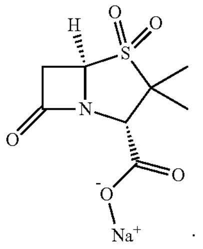

Information about the structure, physicochemical properties and pharmaceutical activity of sulbactam sodium can be found under CAS No. 69388-84-7.

In the present application, the term “avibactam” generally refers to a β-lactamase inhibitor. The chemical name of avibactam may be [(2S,5R)-2-carbamoyl-7-oxo-1, 6-diazabicyclo [3.2.1]oct-6-yl] bisulfate with the following structure:

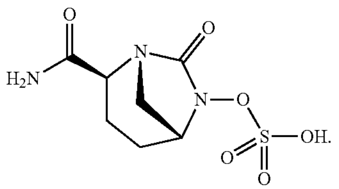

The chemical structure and physicochemical properties of avibactam can be found under CAS No.:1192500-31-4. In the present application, avibactam may form stable pharmaceutically acceptable acid or base salts, in which case it may be appropriate to administer the compound in the form of salt to patients. The term “avibactam or a pharmaceutically acceptable salt thereof” used in the present application also includes any physical form thereof, such as crystalline or amorphous, stereoisomeric and optically active form. For example, commonly used pharmaceutically acceptable salts of avibactam may include avibactam sodium and/or avibactam calcium.

In the present application, the term “avibactam sodium” generally refers to a compound with the structural formula of:

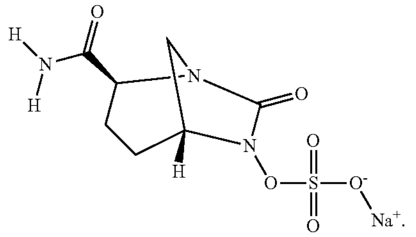

Information about the structure, physicochemical properties and pharmaceutical activity of avibactam sodium can be found under CAS No. 1192491-61-4.

In the present application, the term “pharmaceutically acceptable salt” generally refers to a salt that includes a salt commonly used to form an alkali metal salt and to form an addition salt of a free acid or free base. The nature of the salt is not critical as long as it is pharmaceutically usable. Said pharmaceutically acceptable salts may also include those salts that are, based on reasonable medical judgment, suitable for use when coming into contact with the tissues of a patient and without undue toxicity, irritation, allergic reaction, etc., and those with the reasonable benefit/risk ratio. Suitable pharmaceutically acceptable acid addition salts of the compounds may be prepared from mineral acids or from organic acids. Examples of such mineral acids may be selected from hydrochloric acid, hydrobromic acid, hydroiodic acid, nitric acid, carbonic acid, sulfuric acid and phosphoric acid. Suitable organic acids can be selected from aliphatic, cycloaliphatic, aromatic, aromatic aliphatic, heterocyclic, carboxylic or sulfonic classes of organic acids. Examples may include formic acid, acetic acid, fatty acid, butyric acid, propionic acid, succinic acid, glycolic acid, gluconic acid, lactic acid, malic acid, tartaric acid, citric acid, ascorbic acid, glucuronic acid, maleic acid, fumaric acid, pyruvic acid, aspartic acid, glutamic acid, benzoic acid, anthranilic acid, methanesulfonic acid, 4-hydroxybenzoic acid, phenylacetic acid, mandelic acid, pamoic acid, ethanesulfonic acid, ethanedisulfonic acid, benzenesulfonic acid, pantothenic acid, 2-hydroxytaurine, p-toluenesulfonic acid, p-aminobenesulfonic acid, cyclohexyl aminesulfonic acid, camphanic acid, camphor sulfonic acid, digluconic acid, cyclopentane propionic acid, dodecyl sulfonic acid, glucoheptonic acid, phosphoglycolic acid, heptanoic acid, hexanoic acid, 2-hydroxyethanesulphonic acid, niacin, 2-naphthalene sulfonic acid, oxalic acid, palmitic acid, pectinic acid, persulphuric acid, 2-phenylpropionic acid, picric acid, nevalerate propionic acid, succinic acid, tartaric acid, thiocyanic acid, undecanoic acid, stearic acid, alginic acid, β-hydroxybutyric acid, salicylic acid, galactaric acid and galacturonic acid. Suitable pharmaceutically acceptable base addition salts of the compounds may include metallic salts, such as salts prepared from aluminum, calcium, lithium, magnesium, potassium, sodium, and zinc, or salts prepared from organic bases, and said organic bases which may include primary, secondary, and tertiary amines, substituted amines, including cyclic amines, such as caffeine, arginine, diethylamine, N-ethyl piperidine, aistidine, glucosamine, isopropyl amine, lysine, morpholine, N-ethyl morpholine, piperazine, piperidine, triethylamine and trimethylamine. All such salts may be prepared from the compounds by conventional methods by, for example, reacting a suitable acid or base with the corresponding compound of the present application (avibactam or sulbactam). Once the pharmaceutical composition has been formulated, it can be stored in sterile vials as a solution, suspension, gel, emulsion, solid or dehydrated or lyophilized powder. Such preparations may be stored as ready-to-use forms or as forms that require reconstitution prior to administration (e.g., lyophilized forms). A non-toxic pharmaceutically acceptable salt is preferred, although other salts may also be useful, for example, for isolating or purifying the product.

The salt may be formed by conventional means, such as by allowing the free base form of the product to react with one or more equivalents of an appropriate acid in a solvent or medium or a solvent which is insoluble of salt such as water. The organosilicon is removed either in a vacuum or by freeze-drying, or by exchanging the anion of the existing salt for another anion on a suitable ion-exchange resin.

The synthesis of optically active compounds may be carried out by standard techniques of organic chemistry well known in the art, for example, by synthesis of optically active raw materials or by synthesis of racemic forms. The racemate can be separated into individual enantiomers using known methods (See Advanced Organic Chemistry, Third Edition, Author: J March, pi 04-107). Suitable methods include the formation of diastereomeric derivatives by reaction of racemic substances with chiral auxiliaries, followed by, for example, separation of the diastereomers by chromatography and then by cleavage of the auxiliaries.

The stereoisomers may be separated using conventional techniques such as chromatography or fractional crystallization. The enantiomers can be separated by, for example, separation of the racemate by fractional crystallization, resolution, or HPLC. Diastereomers can be separated by the separation of different physical properties of the diastereomers, e.g., by fractional crystallization, HPLC or flash chromatography. Alternatively, specific stereoisomers can be prepared by chiral synthesis from chiral starting materials under conditions that do not cause racemization or epimerization or by derivatization with chiral reagents.

In the present application, the term "pharmaceutically acceptable carrier" generally refers to one or more non-toxic materials that do not interfere with the biological activity or effectiveness of the active ingredient. The pharmaceutically acceptable carrier may contain salts, buffers, preservatives, compatible carriers, and, optionally, other therapeutic agents. Such pharmaceutically acceptable carriers can also conventionally contain compatible solid or liquid fillers, diluents or encapsulating substances suitable for human administration. For example, a pharmaceutically acceptable carrier may include a flavoring agent, an antimicrobial agent, a sweetener, an antioxidant, an antistatic agent, a lipid, a protein excipient, and/or a salt-forming balancing ion.

In the present application, the term "unit dose" generally refers to physically separated units of a pharmaceutical composition that is suitable for administration as a single dose to a patient, with each unit of it containing a predetermined amount of an active ingredient (e.g., sulbactam or a pharmaceutically acceptable salt thereof, and/or avibactam or a pharmaceutically acceptable salt thereof) calculated to be capable of producing the desired therapeutic effect together with a desired pharmaceutical carrier, diluent, or excipient. In the present application, a "unit dose" of a pharmaceutical composition may be administered to a patient in a single dose. In the present application, the pharmaceutical composition may be prepared to contain an integral number (e.g., one, two, three, or more) of a "unit dose" of strength. In the present application, the pharmaceutical compositions may be prepared to contain ½, ⅓, ¼ of a "unit dose", or other strengths that are less than a "unit dose". In the present application, the pharmaceutical composition can generally be prepared to contain one "unit dose" of strength in order to be suitable for administration. For example, in the present application, said pharmaceutical composition may be prepared to contain one "unit dose" of strength, and the unit dose is expressed in mass. For example, the pharmaceutical composition may comprise an active ingredient (e.g., sulbactam or a pharmaceutically acceptable salt thereof and/or avibactam or a pharmaceutically acceptable salt thereof) with the mass for administering a single dose. For example, the pharmaceutical composition may comprise an active ingredient (e.g., sulbactam or a pharmaceutically acceptable salt thereof and/or avibactam or a pharmaceutically acceptable salt thereof) with the mass for administering two doses. For example, the pharmaceutical composition may comprise an active ingredient (e.g., sulbactam or a pharmaceutically acceptable salt thereof and/or avibactam or a pharmaceutically acceptable salt thereof) with the mass for administering three doses. For example, the pharmaceutical composition may comprise an active ingredient (e.g., sulbactam or a pharmaceutically acceptable salt thereof and/or avibactam or a pharmaceutically acceptable salt thereof) with the mass for administering the dose for a whole day.

In the present application, the term "administration dosage" generally refers to the amount of the pharmaceutical composition, sulbactam or a pharmaceutically acceptable salt thereof, or avibactam or a pharmaceutically acceptable salt thereof, administered to the patients once (unit dose) or two or more times within a defined time interval (e.g., within one day).

In the present application, the term "dosing interval" generally refers to the time interval between two adjacent doses in a dosing regimen with two or more doses. The dosing interval may be indicated as the time elapsed between two adjacent doses. For example, said pharmaceutical composition may be dosed with the following dosing intervals: every 6 hours, every 6.5 hours, every 7 hours, every 7.5 hours, and every 8 hours.

In the present application, the term "dosing frequency" generally refers to the frequency at which the pharmaceutical compositions disclosed herein are administered over a given time period. The dosing frequency may be indicated as the number of doses dosed within a given time period. For example, said pharmaceutical composition may be administered twice a day, three times a day, and/or four times a day.

In the present application, the term "kit" generally refers to a packaged product that comprises components for administering the pharmaceutical compositions, medicaments, sulbactam or a pharmaceutically acceptable salt thereof, and/or avibactam or a pharmaceutically acceptable salt thereof of the present application to prevent, treat, and/or alleviate bacterial infections. Components of the kit may be contained in separate vials (i.e., kits containing separate portions) or supplied in a single vial. The kit may contain reagents such as buffers, protein stabilizing reagents, control molecules for signal generation system, and testing containers. The kit may also contain instructions for carrying out said method.

In the present application, the term "administering device" may generally include: (i) an infusion module. Said infusion module is used to administer a pharmaceutical composition including an active ingredient to a patient; (ii) a medicament for infusion. Said medicament contains an active ingredient selected from the following group: a pharmaceutical composition of the present application, a medicament, sulbactam or a pharmaceutically acceptable salt thereof and/or avibactam or a pharmaceutically acceptable salt thereof; and (iii) an optional pharmacodynamic monitoring module.

In the present application, the term "(be) used in combination with" generally means that two or more therapeutic agents may be co-administered to the patients in a mixture, simultaneously administered as single agents, or administered sequentially as a single agent in any order.

In the present application, the term "bacterial infection" generally refers to any disorder caused by the proliferation and/or presence of bacteria in a cell or a patient. Bacterial infections can be caused by the toxins and other metabolites produced by the growth and proliferation of bacteria (e.g., pathogenic bacteria).

In the present application, the term "treatment" or "treating" generally refers to a clinical intervention that is intended to alter the natural course of the disease suffered by an individual being treated and can be performed to achieve the prevention or treatment of the disease or intervene in the course of a clinical pathogenesis. Desirable therapeutic effects include, but are not limited to, preventing the occurrence or recurrence of a disease, alleviating symptoms, attenuating any direct or indirect pathological consequences of diseases, preventing metastasis, decreasing the speed of disease progression, ameliorating or modifying the state of disease, and palliating or improving the prognosis. Under some circumstances, a medicament (e.g., the pharmaceutical compositions, medicaments, sulbactam or a pharmaceutically acceptable salt thereof and/or avibactam or a pharmaceutically acceptable salt thereof of the present application) may be used to postpone disease progression or slow down disease progression.

In the present application, the term "prevention" or "preventing" generally refers to the prophylactic administration of a medicament (e.g., the pharmaceutical compositions and medicament of the present application, sulbactam or a pharmaceutically acceptable salt thereof and/or avibactam or a pharmaceutically acceptable salt thereof) to healthy patients to prevent the sudden onset of said diseases and conditions (e.g., bacterial infections) described in the present application. In addition, the term "prevention" refers to the prophylactic administration of the pharmaceutical compositions, medicaments, sulbactam or a pharmaceutically acceptable salt thereof and/or avibactam or a pharmaceutically acceptable salt thereof of the present application to patients in the pre-treatment period. The term "prevention" does not require a 100% probability of eliminating the event. More precisely, it represents a reduced likelihood of an event that may occur in the presence of said compound or method.

In the present application, the term "alleviation" or "alleviating" generally refers to the process of reducing, curtailing, or eliminating the recurrence, onset, or progression of one or more symptoms of an individual's condition through the administration of a medicament (e.g., the pharmaceutical composition, drug, sulbactam or a pharmaceutically acceptable salt thereof and/or avibactam or a pharmaceutically acceptable salt thereof) or a combination of drugs (e.g., the pharmaceutical composition, drug, sulbactam or a pharmaceutically acceptable salt thereof and/or avibactam or a pharmaceutically acceptable salt thereof).

In the present application, the term "one or more other antibacterial agents" generally refers to antibacterial agents (or antibiotics) other than the pharmaceutical composition, drug, sulbactam or a pharmaceutically acceptable salt thereof and/or avibactam or a pharmaceutically acceptable salt thereof of the present application. One or more other antibacterial agents may include polymyxin and/or tigecycline.

In the present application, the term "antibiotic" generally refers to a molecule that can inhibit the growth of or kill microorganisms. The antibiotics may include any molecule that specifically inhibits or eliminates the growth of microorganisms, including viruses, bacteria, fungi, or protozoa, but is not lethal to the host, at specific administration concentrations and dosing intervals. The antibiotics include antibacterial agents, antiviral agents, antifungal agents, and antiprotozoal agents. The antibiotics can be broadly classified into bactericidal (i.e., direct killing) or bacteriostatic ones (i.e., blocking cell division). The antibiotics can be further classified into narrow-spectrum (i.e., affecting only a few bacterial subtypes, e.g., Gram-negative, etc.) or broad-spectrum ones (i.e., affecting extensive subtypes). Examples of antibiotics can include: (i) aminoglycosides, such as amikacin, gentamicin, kanamycin, neomycin, netilmicin, streptomycin, tobramycin, paromycin; (ii) ansamycin, such as geldanamycin, and herbicide herbimycin; (iii) carbapenems, such as loracarpef, (iv) carbapenems, such as ertapenum, doripenem, imipenem/cilastatin and meropenem; (v) the first-generation cephalosporins, such as cefadroxil, cefazolin, cefotaxin, and cefalexin; (vi) the second-generation cephalosporins, such as cefaclor, cefamandole, cefoxitin, cefprozil, cefuroxime; (vi) the third-generation cephalosporins, such as cefixime, cefdinir, ceftoren, cefoperazone, cefotaxime, cefpodoxime, ceftazidime, ceftibuten, ceftizoxime, ceftriaxone; (vii) the fourth-generation cephalosporins, such as cefepime; (viii) the fifth-generation cephalosporins, such as ceftobiprole; (ix) glycopeptides; (ix) glycopeptides such as teicoplanin, vancomycin; (x) macrolides, such as axithromycin, clarithromycin, dirithromycine, erythromycin, roxithromycin, troleandomycin, telithromycin, spectinomycin; (xi) monobactams, such as axtreonam; (xii) penicilins, such as amoxicillin, ampicillin, axlocillin, carbenicillin, cloxacillin, dicloxacillin, flucloxacillin, mezlocillin, meticillin, nafcilin, oxacillin, penicillin, peperacillin, ticarcillin; (xiii) antibiotic polypeptide, such as bacitracin, colistin, polymyxin B; (xiv) quinolones, such as ciprofloxacin, enoxacin, gatifloxacin, levofloxacin, lemefloxacin, moxifloxacin, norfloxacin, orfloxacin, trovafloxacin; (xv) sulfonamides, such as mafenide, prontosil, sulfacetamide, sulfamethizole, sulfanilamide, sulfasalazine, sulfisoxazole, trimethoprim, trimethoprim-sulfamethoxazole (TMP-SMX); (xvi) tetracyclines, such as demeclocycline, doxycycline, minocycline, oxytetracycline, tetracycline, and (xvii) others, such as arspenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin or tinidazole.

In the present application, the term "β-lactam antibiotics" generally refers to antibiotics that include a β-lactam mother nucleus in the molecular structure. The antibacterial effect of β-lactam antibiotics is mainly achieved by inhibiting the formation of peptidoglycan in the bacterial cell wall. Examples of common β-lactam antibiotics are: penicillins (e.g., benzathine penicillin, penicillin G, penicillin V, procaine benzylpenicillin, methicillin, dicloxacillin, flucloxacillin, amoxicillin, ampicillin, compound amoxicillin, azlocillin, carbenicillin, ticarcillin, mezlocillin and/or piperacillin), cephalosporins (e.g., cefalexin, cefalotin, cefazolin, cefaclor, cefuroxime sodium, cefamandole, cefotetan, cefoxitin, ceftriaxone, cefotaxime, ceftazidime, cefepime and/or cefpirome), carbapenems (e.g., imipenem (with cilastatin), meropenem, ertapenem, faropenem and/or biapenem), monoamide cyclics (e.g., aztreonam), β-lactamase inhibitors (e.g., clavulanic acid, tazobactam and/or sulbactam). Some bacteria have developed resistance to β-lactam antibiotics, including using enzymes to hydrolyze the β-lactam ring, using another penicillin-binding protein, or using the "efflux pump" to pump the drug directly out of the bacteria.

Unless otherwise defined in the claims, the term "optionally" used herein means that the event described subsequently may or may not occur and includes both the occurrence and non-occurrence of the event.

DETAILED DESCRIPTION OF THE INVENTION

Pharmaceutical Composition

In one aspect, the present application provides a pharmaceutical composition and said pharmaceutical composition comprises sulbactam or a pharmaceutically acceptable salt thereof and avibactam or a pharmaceutically acceptable salt thereof.

Content

In the present application, unit dose ratio (mass ratio) of sulbactam or a pharmaceutically acceptable salt thereof and avibactam or a pharmaceutically acceptable salt thereof in said pharmaceutical composition may be about 8:1 to about 4:1 (e.g., about 7:1 to about 4:1, about 6:1 to about 4:1, about 5:1 to about 4:1, about 7.5:1, about 7:1, about 6.5:1, about 6:1, about 5.5:1, about 5:1 or about 4.5:1). For example, in the strengths of said pharmaceutical composition, the mass ratio of sulbactam or a pharmaceutically acceptable salt thereof and avibactam or a pharmaceutically acceptable salt thereof may be about 8:1 to about 4:1 (e.g., about 7:1 to about 4:1, about 6:1 to about 4:1, about 5:1 to about 4:1, about 7.5:1, about 7:1, about 6.5:1, about 6:1, about 5.5:1, about 5:1 or about 4.5:1).

For example, the unit dose ratio (mass ratio) of sulbactam or a pharmaceutically acceptable salt thereof and avibactam or a pharmaceutically acceptable salt thereof in the pharmaceutical composition of the present application may be about 8:1. For example, the unit dose ratio (mass ratio) of sulbactam or a pharmaceutically acceptable salt thereof and avibactam or a pharmaceutically acceptable salt thereof in the pharmaceutical composition of the present application may be about 6:1. For example, the unit dose ratio (mass ratio) of sulbactam or a pharmaceutically acceptable salt thereof and avibactam or a pharmaceutically acceptable salt thereof in the pharmaceutical composition of the present application may be about 4:1.

In the present application, unit dose (mass) of sulbactam or a pharmaceutically acceptable salt thereof in said pharmaceutical composition may be about 1 g-4 g (e.g., about 1 g-3.5 g, about 1 g-3 g, about 1 g-2.5 g, about 1 g-2 g, about 1 g-1.5 g, about 1.5 g-4 g, about 2 g-4 g, about 2.5 g-4 g, about 3 g-4 g, about 3.5 g-4 g, about 1 g, about 1.5 g, about 2 g, about 2.5 g, about 3 g, about 3.5 g or about 4 g).

In the present application, unit dose (mass) of avibactam or a pharmaceutically acceptable salt thereof in said pharmaceutical composition may be about 0.125 g-1 g (e.g., about 0.125 g-0.75 g, about 0.125 g-0.5 g, about 0.125 g-0.25 g, about 0.25 g-1 g, about 0.5 g-1 g, about 0.75 g-1 g, about 0.125 g, about 0.25 g, about 0.5 g, about 0.625 g, with about 0.75 g or about 1 g).

For example, the unit dose (mass) of sulbactam or a pharmaceutically acceptable salt thereof in the pharmaceutical composition of the present application may be about 4 g-16 g, and the unit dose (mass) of avibactam or a pharmaceutically acceptable salt thereof may be about 0.5 g-4 g. For example, the unit dose (mass) of sulbactam or a pharmaceutically acceptable salt thereof in the pharmaceutical composition of the present application is about 2 g-8 g, and the unit dose (mass) of avibactam or a pharmaceutically acceptable salt thereof is about 0.25 g-2 g. For example, the unit dose (mass) of sulbactam or a pharmaceutically acceptable salt thereof in the pharmaceutical composition of the present application is about 1 g-4 g, and the unit dose (mass) of avibactam or a pharmaceutically acceptable salt thereof is about 0.125 g-1 g.

For example, the unit dose (mass) of sulbactam or a pharmaceutically acceptable salt thereof in the pharmaceutical composition of the present application is about 8 g, and the unit dose (mass) of avibactam or a pharmaceutically acceptable salt thereof is about 2 g. For example, the unit dose (mass) of sulbactam or a pharmaceutically acceptable salt thereof in the pharmaceutical composition of the present application is about 8 g, and the unit dose (mass) of avibactam or a pharmaceutically acceptable salt thereof is about 1 g. For example, the unit dose (mass) of sulbactam or a pharmaceutically acceptable salt thereof in the pharmaceutical composition of the present application is about 4 g, and the unit dose (mass) of avibactam or a pharmaceutically acceptable salt thereof is about 1 g. For example, the unit dose (mass) of sulbactam or a pharmaceutically acceptable salt thereof in the pharmaceutical composition of the present application is about 8 g, and the unit dose (mass) of avibactam or a pharmaceutically acceptable salt thereof is about 1 g. For example, the unit dose (mass) of sulbactam or a pharmaceutically acceptable salt thereof in the pharmaceutical composition of the present application is about 2 g, and the unit dose (mass) of avibactam or a pharmaceutically acceptable salt thereof is about 0.5 g. For example, the unit dose (mass) of sulbactam or a pharmaceutically acceptable salt thereof in the pharmaceutical composition of the present application is about 1 g, and the unit dose (mass) of avibactam or a pharmaceutically acceptable salt thereof is about 0.25 g.

For example, the unit dose (mass) of sulbactam in the pharmaceutical composition of the present application may be about 4 g-16 g, and the unit dose (mass) of avibactam may be about 0.5 g-4 g. For example, the unit dose (mass) of sulbactam in the pharmaceutical composition of the present application is about 2 g-8 g, and the unit dose (mass) of avibactam is about 0.25 g-2 g. For example, the unit dose (mass) of sulbactam in the pharmaceutical composition of the present application is about 1 g-4 g, and the unit dose (mass) of avibactam is about 0.125 g-1 g.

For example, the unit dose (mass) of sulbactam in the pharmaceutical composition of the present application is about 8 g, and the unit dose (mass) of avibactam is about 2 g. For example, the unit dose (mass) of sulbactam in the pharmaceutical composition of the present application is about 8 g, and the unit dose (mass) of avibactam is about 1 g. For example, the unit dose (mass) of sulbactam in the pharmaceutical composition of the present application is about 4 g, and the unit dose (mass) of avibactam is about 1 g. For example, the unit dose (mass) of sulbactam in the pharmaceutical composition of the present application is about 3 g, and the unit dose (mass) of avibactam is about 0.5 g. For example, the unit dose (mass) of sulbactam in the pharmaceutical composition of the present application is about 2 g, and the unit dose (mass) of avibactam is about 0.5 g. For example, the unit dose (mass) of sulbactam in the pharmaceutical composition of the present application is about 1 g, and the unit dose (mass) of avibactam is about 0.25 g.

In the present application, said pharmaceutical composition may comprise sulbactam and avibactam. In the present application, said pharmaceutical composition may comprise sulbactam and avibactam sodium. In the present application, said pharmaceutical composition may comprise sulbactam sodium and avibactam. In the present application, said pharmaceutical composition may comprise sulbactam sodium and avibactam sodium. In the present application, said pharmaceutical composition may comprise sulbactam and avibactam calcium. In the present application, said pharmaceutical composition may comprise sulbactam calcium and avibactam. In the present application, said pharmaceutical composition may comprise sulbactam calcium and avibactam calcium. In the present application, said pharmaceutical composition may comprise sulbactam calcium and avibactam sodium. In the present application, said pharmaceutical composition may comprise sulbactam sodium and avibactam calcium.

For example, in the pharmaceutical composition of the present application, unit dose (mass) of sulbactam sodium may be about 4 g-16 g, and unit dose (mass) of avibactam sodium may be about 0.5 g-4 g. For example, the unit dose (mass) of sulbactam sodium in the pharmaceutical composition of the present application is about 2 g-8 g, and the unit dose (mass) of avibactam sodium is about 0.25 g-2 g. For example, the unit dose (mass) of sulbactam sodium in the pharmaceutical composition of the present application is about 1 g-4 g, and the unit dose (mass) of avibactam sodium is about 0.125 g-1 g.

For example, the unit dose (mass) of sulbactam sodium in the pharmaceutical composition of the present application is about 8 g and the unit dose (mass) of avibactam sodium is about 2 g. For example, the unit dose (mass) of sulbactam sodium in the pharmaceutical composition of the present application is about 8 g and the unit dose (mass) of avibactam sodium is about 1 g. For example, the unit dose (mass) of sulbactam sodium in the pharmaceutical composition of the present application is about 4 g and the unit dose (mass) of avibactam sodium is about 1 g. For example, the unit dose (mass) of sulbactam sodium in the pharmaceutical composition of the present application is about 3 g, and the unit dose (mass) of avibactam sodium is about 0.5 g. For example, the unit dose (mass) of sulbactam sodium in the pharmaceutical composition of the present application is about 2 g, and the unit dose (mass) of avibactam sodium is about 0.5 g. For example, the unit dose (mass) of sulbactam sodium in the pharmaceutical composition of the present application is about 1 g, and the unit dose (mass) of avibactam sodium is about 0.25 g.

For example, in said pharmaceutical composition, the unit dose (mass) of said sulbactam or the pharmaceutically acceptable salt thereof may be about 1 g-4 g, the unit dose (mass) of said avibactam or the pharmaceutically acceptable salt thereof may be about 0.125 g-1 g, and the unit dose ratio of said sulbactam or the pharmaceutically acceptable salt thereof and said avibactam or the pharmaceutically acceptable salt thereof is about 4:1.

Formulation

In said pharmaceutical composition, said sulbactam or the pharmaceutically acceptable salt thereof and said avibactam or the pharmaceutically acceptable salt thereof may co-exist in a container, a package or any other space for physical separation, i.e., the two are mixed in physical morphology. In said pharmaceutical composition, said sulbactam or the pharmaceutically acceptable salt thereof and said avibactam or the pharmaceutically acceptable salt thereof may exist independently in different containers, packages, or any other space for physical separation (physically separated).

The pharmaceutical composition of the present application may also optionally comprise a pharmaceutically acceptable carrier. Said pharmaceutically acceptable carrier is non-toxic to the recipient at the doses and concentrations employed and may include buffers, antioxidants, preservatives, low-molecular-weight (less than about 10 residues) polypeptides, proteins, hydrophilic polymers, amino acids, carbohydrates, salt-forming counter ions, metal complexes, and/or non-ionic surfactants.

The pharmaceutical composition of the application may also contain more than one other active compound, which usually does not adversely affect the activity of sulbactam or its pharmaceutically acceptable salt and/or avibactam or its pharmaceutically acceptable salt. For example, the pharmaceutical composition of the present application may further comprise polymyxin. The pharmaceutical composition of the present application may further comprise tigecycline.

The pharmaceutical compositions of the present application may be administered parenterally, by injection or orally. Said administration via injection may include routes of administrations such as intravenous injection, intramuscular injection, intraperitoneal injection, intradermal injection or subcutaneous injection. Said pharmaceutical compositions comprise various dosage forms that are conventional in the field, for example, the dosage form of solid, semi-solid or liquid, may be in the form of aqueous solution, non-aqueous solution or suspension, and may also be in the form of tablets, capsules, granules, injections or infusions. For example, said pharmaceutical composition may be prepared as a liquid. For example, said pharmaceutical composition may be prepared as a solid, and the solid may be dissolved as a liquid for use.

For example, said pharmaceutical composition may comprise a pH adjusting agent such that its pH is about 4 to about 8. For example, said pharmaceutical composition may have a pH about 5 to about 8. For example, said pharmaceutical composition may have a pH about 5 to about 7.5. For example, said pharmaceutical composition may have a pH about 5 to about 7.3. For example, said pharmaceutical composition may have a pH about 5 to about 7. For example, said pharmaceutical composition may have a pH about 5 to about 6.5. For example, said pharmaceutical composition may have a pH about 5 to about 6. For example, said pharmaceutical composition may have a pH about 5.5 to about 7.3. For example, said pharmaceutical composition may have a pH about 6 to about 7.3.

In the present application, said pharmaceutical compositions may be used in combination with one or more other antibacterial agents. For example, said pharmaceutical composition may be used in combination with polymyxin. For example, said pharmaceutical composition may be used in combination with tigecycline.

Treatment Methods

In one aspect, the present invention provides a method for preventing, treating and/or alleviating bacterial infections and said method comprises administering to a patient in need thereof the pharmaceutical composition of the present application.

The present application provides said pharmaceutical compositions for use in the prevention, treatment and/or alleviation of bacterial infections.

Indications

In the present application, said bacterial infections may comprise infections caused by Gram-negative bacteria. For example, said bacterial infections may be caused by one or more pathogens that express one or more β-lactamases. For example, said bacterial infections may be caused by one or more pathogens expressing one or more type A, C, and/or D β-lactamases. For example, said bacterial infections may be caused by the *Acinetobacter* genus. For example, said bacterial infections may be caused by *Pseudomonas aeruginosa*. For example, said bacterial infections may be caused by enterobacteriaceae. For example, said bacterial infection may be caused by *Burkholderia* spp.

For example, said bacterial infections may be caused by *Acinetobacter baumannii*. For example, said *Acinetobacter baumannii* genus may comprise *Acinetobacter baumannii* that expresses one or more type A, C, and/or D β-lactamases. For example, said *Acinetobacter baumannii* genus may comprise *Acinetobacter baumannii* that expresses one or more type A β-lactamases. For example, said *Acinetobacter baumannii* genus may comprise *Acinetobacter baumannii* that expresses one or more type C β-lactamases. For example, said *Acinetobacter baumannii* genus may comprise *Acinetobacter baumannii* that expresses one or more type D β-lactamases. For example, said *Acinetobacter baumannii* genus may comprise *Acinetobacter baumannii* that expresses TEM-1 or KPC-2.

In the present application, said bacterial infections may comprise infections caused by drug-resistant strains. For example, said bacterial infections may comprise an infection caused by a drug-resistant strain, and said bacterium is resistant to cephalosporins. For example, said bacterial infections may comprise an infection caused by a drug-resistant strain, and said bacterium is resistant to carbapenems. For example, said bacterial infections may comprise an infection caused by a drug-resistant strain, and said bacterium is resistant to fluoroquinolones. For example, said bacterial infections may comprise an infection caused by a drug-resistant strain, and said bacterium is resistant to aminoglycoside. For example, said bacterial infections may comprise an infection caused by a drug-resistant strain, and said bacterium is resistant to cefoperazone. For example, said bacterial infections may comprise an infection caused by a drug-resistant strain, and said bacterium is resistant to amikacin. For example, said bacterial infections may comprise an infection caused by a drug-resistant strain, and said bacterium is resistant to levofloxacin. For example, said bacterial infections may comprise an infection caused by a drug-resistant strain, and said bacterium is resistant to sulbactam. For example, said bacterial infections may comprise an infection caused by a drug-resistant strain, and said bacterium is resistant to minocycline.

In the present application, said bacterial infections may comprise a respiratory tract infection, a bloodstream infection, an intra-abdominal infection, a skin and soft tissue infection, a urinary system infection, and/or a central nervous system infection. For example, said bacterial infection may be a respiratory tract infection. For example, said bacterial infection may be a bloodstream infection. For example, said bacterial infection may be an intra-abdominal infection. For example, said bacterial infection may be a skin and soft tissue infection. For example, said bacterial infection may be a urinary system infection. For example, said bacterial infection may be a central nervous system infection. For example, said bacterial infection may be a lung infection. For example, said bacterial infection may be pneumonia.

For example, said bacterial infection may be a lung infection caused by *Acinetobacter baumannii.*

In one aspect, the present application provides a method for preventing, treating and/or alleviating an infection caused by *Acinetobacter baumannii* and said method comprises administering to a patient in need thereof the pharmaceutical composition of the present application.

In one aspect, the present application provides a method for preventing, treating and/or alleviating pneumonia caused by *Acinetobacter baumannii*, and said method comprises administering to a patient in need thereof the pharmaceutical composition of the present application.

Embodiment Modes

In the present application, with respect to the prevention, treatment, and/or alleviation of bacterial infections as previously mentioned in said pharmaceutical composition, the ratio of administration dosage of sulbactam or a pharmaceutically acceptable salt thereof to avibactam or a pharmaceutically acceptable salt thereof may be about 8:1-4:1 (e.g., about 7:1 to about 4:1, about 6:1 to about 4:1, about 5:1 to about 4:1, about 7.5:1, about 7:1, about 6.5:1, about 6:1, about 5.5:1, about 5:1 or about 4.5:1). For example, the ratio of the administration dosages of sulbactam or a pharmaceutically acceptable salt thereof to avibactam or a pharmaceutically acceptable salt thereof may be about 8:1. For example, the ratio of the administration dosages of sulbactam or a pharmaceutically acceptable salt thereof to avibactam or a pharmaceutically acceptable salt thereof may be about 6:1. For example, the ratio of the administration dosages of sulbactam or a pharmaceutically acceptable salt thereof to avibactam or a pharmaceutically acceptable salt thereof may be about 4:1. Said administration dosage may be the total amount of drug used over a certain period of time (e.g., in one day) or the amount of drug administered at one time.

For example, in the pharmaceutical composition of the present application, the administration dosage of sulbactam or a pharmaceutically acceptable salt thereof may be about 4 g-12 g/day, and the administration dosage of avibactam or a pharmaceutically acceptable salt thereof may be about 0.5 g-3 g/day. For example, in the pharmaceutical composition of the present application, the administration dosage of sulbactam or a pharmaceutically acceptable salt thereof may be about 4 g-8 g/day, and the administration dosage of avibactam or a pharmaceutically acceptable salt thereof may be about 1 g-2 g/day. For example, in the pharmaceutical composition of the present application, the administration dosage of sulbactam or a pharmaceutically acceptable salt thereof may be about 8 g-12 g/day, and the administration dosage of avibactam or a pharmaceutically acceptable salt thereof may be about 2 g-3 g/day.

For example, in the pharmaceutical composition of the present application, the administration dosage of sulbactam or a pharmaceutically acceptable salt thereof may be about 4 g-12 g/day, and the administration dosage of avibactam or a pharmaceutically acceptable salt thereof may be about 0.5 g-3 g/day and the ratio of administration dosage of sulbactam or a pharmaceutically acceptable salt thereof to avibactam or a pharmaceutically acceptable salt thereof may be about 4:1. For example, in the pharmaceutical composition of the present application, the administration dosage of sulbactam or a pharmaceutically acceptable salt thereof may be about 4 g-8 g/day, and the administration dosage of avibactam or a pharmaceutically acceptable salt thereof may be about 0.5 g-2 g/day, and the ratio of administration dosage of sulbactam or a pharmaceutically acceptable salt thereof to avibactam or a pharmaceutically acceptable salt thereof may be about 4:1. For example, in the pharmaceutical composition of the present application, the administration dosage of sulbactam or a pharmaceutically acceptable salt thereof may be about 8 g-12 g/day, and the administration dosage of avibactam or a pharmaceutically acceptable salt thereof may be about 2 g-3 g/day, and the ratio of the administration dosage of sulbactam or a pharmaceutically acceptable salt thereof to avibactam or a pharmaceutically acceptable salt thereof may be about 4:1.

For example, in the pharmaceutical composition of the present application, the administration dosage of sulbactam or a pharmaceutically acceptable salt thereof is about 12 g per day, and the administration dosage of avibactam or a pharmaceutically acceptable salt thereof is about 3 g per day. For example, the dosage of sulbactam or a pharmaceutically acceptable salt thereof in the pharmaceutical composition of the present application is about 8 g per day and the dosage of avibactam or a pharmaceutically acceptable salt thereof is about 2 g per day. For example, in the pharmaceutical composition of the present application, the administration dosage of sulbactam or a pharmaceutically acceptable salt thereof may be about 6 g/day, and the administration dosage of avibactam or a pharmaceutically acceptable salt thereof may be about 1.5 g/day. For example, the dosage of sulbactam or a pharmaceutically acceptable salt thereof in the pharmaceutical composition of the present application is about 4 g per day and the dosage of avibactam or a pharmaceutically acceptable salt thereof is about 1 g per day.

In the present application, dosing interval of said pharmaceutical composition may be about every 6 hours-8 hours, 2 times-4 times daily, and the administration dosage is about 1 g-3 g each time for sulbactam or a pharmaceutically acceptable salt thereof and about 0.25 g-1 g each time for avibactam or a pharmaceutically acceptable salt thereof.

In the present application, the dosing interval of said pharmaceutical composition may be about every 6 hours, 4 times daily, and the administration dosage is about 1 g-3 g each time for sulbactam or a pharmaceutically acceptable salt thereof and about 0.25 g-1 g each time for avibactam or a pharmaceutically acceptable salt thereof. In the present application, the dosing interval of said pharmaceutical composition may be about every 6 hours, 4 times daily, and the administration dosage is about 1 g-2 g each time for sulbactam or a pharmaceutically acceptable salt thereof and about 0.25 g-0.5 g each time for avibactam or a pharmaceutically acceptable salt thereof.

In the present application, the dosing interval of said pharmaceutical composition may be about every 8 hours, 3 times daily, and the administration dosage is about 1 g-3 g each time for sulbactam or a pharmaceutically acceptable salt thereof and about 0.25 g-1 g each time for avibactam or a pharmaceutically acceptable salt thereof.

In the present application, the dosing interval of said pharmaceutical composition may be about every 12 hours, 2 times daily, and the administration dosage is about 1 g-3 g each time for sulbactam or a pharmaceutically acceptable salt thereof and about 0.25 g-1 g each time for avibactam or a pharmaceutically acceptable salt thereof. In the present application, the dosing interval of said pharmaceutical composition may be about every 12 hours, 2 times daily, and the administration dosage is about 2 g-3 g each time for sulbactam or a pharmaceutically acceptable salt thereof and about 0.5 g-1 g each time for avibactam or a pharmaceutically acceptable salt thereof.

For example, the dosing interval of said pharmaceutical composition may be about every 12 hours, 2 times daily, and the administration dosage is about 4 g each time for sulbactam or a pharmaceutically acceptable salt thereof and about 1 g each time for avibactam or a pharmaceutically acceptable salt thereof.

For example, the dosing interval of said pharmaceutical composition may be about every 6 hours, 4 times daily, and the administration dosage is about 2 g each time for sulbactam or a pharmaceutically acceptable salt thereof and about 0.5 g each time for avibactam or a pharmaceutically acceptable salt thereof.

For example, the dosing interval of said pharmaceutical composition may be about every 8 hours, 3 times daily, and the administration dosage is about 2 g each time for sulbactam or a pharmaceutically acceptable salt thereof and about 0.5 g each time for avibactam or a pharmaceutically acceptable salt thereof.

In the present application, said sulbactam or the pharmaceutically acceptable salt thereof and said avibactam or the pharmaceutically acceptable salt thereof may be administered separately or simultaneously. The separate administration of said sulbactam or the pharmaceutically acceptable salt thereof and said avibactam or the pharmaceutically acceptable salt thereof comprises sequential administration of said sulbactam or the pharmaceutically acceptable salt thereof and said avibactam or the pharmaceutically acceptable salt thereof in any order of administration. The simultaneous administration of said sulbactam or the pharmaceutically acceptable salt thereof together with said avibactam or the pharmaceutically acceptable salt thereof comprises simultaneous administration of said sulbactam and said avibactam as part of a pharmaceutical composition of the two drugs or as the pharmaceutical composition of the two drugs simultaneous administered for at least part of the total administration time.

In the present application, said method may further comprise administering one or more other antibacterial agents. For example, said pharmaceutical composition may be used in combination with one or more other antibacterial agents. For example, said pharmaceutical composition may be administered prior to the use of one or more other antibacterial agents. For example, said pharmaceutical composition may be administered simultaneously with one or more other antibacterial agents. For example, said pharmaceutical composition may be administered after the administration of one or more other antibacterial agents.

In another aspect, the present application provides a method for preventing, treating, and/or alleviating an *Acinetobacter baumannii* infection, and said method comprises administering to a patient in need thereof sulbactam or a pharmaceutically acceptable salt thereof and avibactam or a pharmaceutically acceptable salt thereof, and ratio of administration dosage of said sulbactam or the pharmaceutically acceptable salt thereof to said avibactam or the pharmaceutically acceptable salt thereof is about 8:1 to about 4:1 (e.g., about 4:1).

In another aspect, the present application provides a method for preventing, treating and/or alleviating an *Acinetobacter baumannii* infection, and said method comprises administering to a patient in need thereof sulbactam or a pharmaceutically acceptable salt thereof and avibactam or a pharmaceutically acceptable salt thereof, ratio of administration dosage of said sulbactam or the pharmaceutically acceptable salt thereof to said avibactam or the pharmaceutically acceptable salt thereof is about 8:1 to about 4:1 (e.g., about 4:1), and dosing interval, dosing frequency, and administration dosage can meet the following condition: during more than 40% of the period of the dosing interval, plasma concentrations of these two drugs are greater than their respective minimum inhibitory concentrations (e.g., $MIC_{90}$).

In another aspect, the present application provides a method for preventing, treating and/or alleviating an *Acinetobacter baumannii* infection, and said method comprises administering to a patient in need thereof sulbactam or a pharmaceutically acceptable salt thereof and avibactam or a pharmaceutically acceptable salt thereof, ratio of administration dosage of said sulbactam or the pharmaceutically acceptable salt thereof to said avibactam or the pharmaceutically acceptable salt thereof is about 8:1 to about 4:1 (e.g., about 4:1) and the administration dosage of said sulbactam or the pharmaceutically acceptable salt thereof is about 4 g-12 g/day, and the administration dosage of said avibactam or the pharmaceutically acceptable salt thereof is about 0.5 g-3 g/day.

In another aspect, the present application provides a method for preventing, treating and/or alleviating an *Acinetobacter baumannii* infection and said method comprises administering to a patient in need thereof sulbactam or a pharmaceutically acceptable salt thereof and avibactam or a pharmaceutically acceptable salt thereof, and administration dosage of said sulbactam or the pharmaceutically acceptable salt thereof is about 8 g/day and administration dosage of said avibactam or the pharmaceutically acceptable salt thereof is about 2 g/day.

In another aspect, the present application provides a method for preventing, treating and/or alleviating an *Acinetobacter baumannii* infection and said method comprises administering to a patient in need thereof sulbactam or a pharmaceutically acceptable salt thereof and avibactam or a pharmaceutically acceptable salt thereof, and administration dosage of said sulbactam or the pharmaceutically acceptable salt thereof is about 8 g/day, administration dosage of said avibactam or the pharmaceutically acceptable salt thereof is about 2 g/day, and dosing intervals of the two drugs are every 6 hours-8 hours.

Without intending to be limited by any theory, the following examples are only to explain the various technical solutions of the present application invention and are not used to limit the scope of the present application invention.

EXAMPLES

Example 1: Determination of Minimum Inhibitory Concentration of Sulbactam Sodium and Avibactam Sodium Against Clinical Strains of *Acinetobacter baumannii*

The minimum inhibitory concentration (MIC) was determined in accordance with the requirements of the Clinical and Laboratory Standards Institute (CLSI) M07 (for aerobic bacteria).

TABLE 1

| Test Drugs (Combinations) | | |
|---|---|---|
| Compounds (combination) | Maximum concentration (μg/mL) | Minimum concentration (μg/mL) |
| Sulbactam sodium | 64 | 0.06 |
| Avibactam sodium | 32 | 0.5 |

2. Test Strains

TABLE 2

| Test Strains (10 Clinical Strains) | | |
|---|---|---|
| Bacterial name | Strain No. | Culturing medium |
| *Acinetobacter baumannii* | ATCC 19606 | a |
| *Acinetobacter baumannii* | TNP041702 | a |
| *Acinetobacter baumannii* | TNP041703 | a |
| *Acinetobacter baumannii* | TNP041704 | a |
| *Acinetobacter baumannii* | TNP041705 | a |
| *Acinetobacter baumannii* | TNP041706 | a |
| *Acinetobacter baumannii* | TNP041707 | a |
| *Acinetobacter baumannii* | TNP041708 | a |
| *Acinetobacter baumannii* | TNP041709 | a |
| *Acinetobacter baumannii* | TNP041710 | a |
| *Acinetobacter baumannii* | TNP041711 | a |

Medium: a = CAMHB (cation adjusted Mueller-Hinton medium).

TABLE 3

Information of Drug Resistance of 10 Clinical Strains

| β- Gene sequence of lactamase | Strain No. | | | | | | | | | |
|---|---|---|---|---|---|---|---|---|---|---|
| | TNP 041702 VIM, AmpC, Oxa23-1, Oxa48, Oxa51 | TNP 041703 AmpC, Oxa23-1, Oxa23-2, Oxa48, Oxa51 | TNP 041704 AmpC, Oxa23-1, Oxa23-2, Oxa24, Oxa51, Oxa64 | TNP 041705 VIM, AmpC, Oxa23-1, Oxa23-2, Oxa24, Oxa51, Oxa64 | TNP 041706 VIM, AmpC, Oxa23-1, Oxa51 | TNP 041707 KPC, VIM, AmpC, Oxa23-1, Oxa48, Oxa51, Oxa58, Oxa64 | TNP 041708 KPC, VIM, AmpC, Oxa23-1, Oxa23-2, Oxa48, Oxa58, Oxa64 | TNP 041709 VIM, Oxa23-1, Oxa48, Oxa51 | TNP 041710 Oxa23-1, Oxa23-2, Oxa24, Oxa51, Oxa64 | TNP 041711 VIM, AmpC, Oxa23-1, Oxa23-2, Oxa24, Oxa51, Oxa58, Oxa64 |
| Amikacin | R | R | R | R | S | R | S | R | R | R |
| Gentamicin | R | R | R | R | S | R | R | R | R | R |
| Piperacillin | R | R | R | R | R | R | R | R | R | R |
| Cefazolin | R | R | R | R | R | R | R | R | R | R |
| Cefuroxime | R | R | R | R | R | R | R | R | R | R |
| Cefotaxime | R | R | R | R | R | R | R | R | R | R |
| Ceftazidime | R | R | R | R | R | R | R | R | R | R |
| Cefepime | R | R | R | R | R | R | R | R | R | R |
| Ciprofloxacin | R | R | R | R | R | R | R | R | R | R |
| Trimethoprim/ sulfamethoxazole | R | R | R | R | R | I | R | R | R | R |
| Cefoperazone-sulbactam | R | R | I | R | R | R | R | I | R | I |
| Piperacillin-tazobactam | R | R | R | R | R | R | R | R | R | R |
| Imipenem | R | R | R | R | R | R | R | R | R | R |
| Meropenem | R | R | R | R | R | R | R | R | R | R |

S: Drug Susceptible, I: Drug Intermediate, R: Drug Resistant

3. Experimental Steps 3.1 The compounds were diluted with water up to 100 times of the highest concentration tested.

3.2 The compounds were diluted in a 2-fold gradient, depending on the compounds' solubility. The dilution steps are as follows: first dilute the compounds or antibiotics to 100 times of the highest final concentration tested, and then:

A 50 μL of sterile water and 50 μL of sulbactam sodium mother liquid were added into the first column of the first 96-well plate, and 50 μL of water was added into each of the remaining wells; then 50 μL of liquid was pipetted from the $1^{st}$ column and added into the $2^{nd}$ column; after being pipetted up and down to even, 50 μL of the liquid was pipetted and added to the $3^{rd}$ column, and then it was diluted in 2-fold gradient in sequence for a total of 10 times and then 50 μL was removed from each well of the $11^{th}$ column to obtain the compound solution diluted to a 2-fold gradient; and then 4 μL of the solution was transferred to a 96-well test plate.

A 50 μL of sterile water and 50 μL of avibactam sodium mother liquid were added into the A row of the second 96-well plate, and 50 μL of water was added into each of the remaining wells. A 50 μL of liquid was pipetted from the A row and added into the B row; after being pipetted up and down to even, 50 μL of the solution was pipetted and added to the C row, and diluted in a 2-fold gradient in turn for a total of 6 times and then, 50 μL was removed from each well of the G row to obtain the compound solution diluted to a 2-fold gradient and then 4 μL was transferred to a 96-well test plate.

3.3 Preparation of Strain Inoculums:

Aerobic bacteria: the strains were inoculated on MHA one day in advance and incubated overnight at 37° C. On the day of the assay, 5-6 single colonies were picked and suspended evenly in saline, and the bacterial concentration was adjusted to the turbidity of 0.5 McFarland standard (concentration is about $1\times10^8$ CFU/mL). The bacterial suspension was diluted 200 times with the corresponding liquid culture medium (Table 1), i.e., at a bacterial concentration of ~$5\times10^5$ CFU/ml, then 192 μL was transferred to a 96-well round bottom plate to obtain the test plate. Then, the 96-well round bottom plate obtained above was placed into an incubator at 37° C. and 85% humidity to incubate for 20 h.

3.4 Determination of MIC: the lowest concentration of the compound at which the bacterial growth is completely or significantly inhibited by visual inspection will be defined as the MIC of the compound. When sulbactam is used in combination with avibactam, the lowest concentration of the compound represents the sum of the concentrations of the two compounds.

The results are shown in Table 4. The results showed that when the mass ratio of sulbactam sodium to avibactam sodium was 4:1 and 8:1, the MIC was lower than that when sulbactam sodium or avibactam sodium were administered alone, also lower than that when the mass ratio of sulbactam sodium to avibactam sodium was 2:1. The results showed that the antibacterial effect of sulbactam sodium and avibactam sodium was superior when they were administered at the mass ratio of 4:1 and 8:1 than that of sulbactam sodium or avibactam sodium was administered alone, and the antibacterial effect was also superior than that of sulbactam sodium and avibactam sodium administered at the mass ratio of 2:1 ($MIC_{90}$ was 24 μg/mL). The results of MIC data indicated that when the sulbactam sodium and avibactam sodium were administered at a mass ratio of 4:1, the $MIC_{90}$ of sulbactam and avibactam sodium was 20 μg/mL; when the sulbactam sodium and avibactam sodium were administered at a mass ratio of 8:1, the $MIC_{90}$ of sulbactam and avibactam was 18 μg/mL, which could effectively reduce the administration dosage of sulbactam sodium and avibactam sodium to about ¼, and improve the safety at the same effective dose.

TABLE 4

| Minimum Inhibitory Concentration of the Pharmaceutical Composition of Sulbactam Sodium and Avibactam Sodium against the of Clinical Strains of *Acinetobacter baumannii* | | | |
|---|---|---|---|
| Drug (Combination) | MIC range (μg/mL) | $MIC_{50}$ (μg/mL) | $MIC_{90}$ (μg/mL) |
| Sulbactam sodium | 8-32 | 32 | 32 |
| Avibactam sodium | >32 | >32 | >32 |
| Sulbactam sodium/avibactam sodium = 2:1 | 6-24 | 12 | 24 |
| Sulbactam sodium/avibactam sodium = 4:1 | 10-20 | 10 | 20 |
| Sulbactam sodium/avibactam sodium = 8:1 | 9-36 | 9 | 18 |

Example 2: Determination of Minimum Inhibitory Concentration of Sulbactam Sodium and Avibactam Sodium Against *Acinetobacter baumannii* Strains The minimum inhibitory concentration (MIC) was determined in accordance with the requirements of the Clinical and Laboratory Standards Institute (CLSI) M07 (for aerobic bacteria).

1. Test Drugs (Combination)

TABLE 5

| Test Drugs (Combinations) | | |
|---|---|---|
| Compounds (combination) | Maximum concentration (μg/mL) | Minimum concentration (μg/mL) |
| Sulbactam sodium | 128 | 0.125 |
| Avibactam sodium | 128 | 0.125 |
| Sulbactam sodium/avibactam sodium = 1: 1 | 64 + 64 | 0.063 + 0.063 |
| Sulbactam sodium/avibactam sodium = 2:1 | 64 + 32 | 0.063 + 0.031 |
| Sulbactam sodium/avibactam sodium = 4:1 | 64 + 16 | 0.063 + 0.016 |
| Tigecycline | 32 | 0.031 |
| Polymyxin | 32 | 0.031 |

2. Test Strains

TABLE 6

| Test Strains (20 Total Strains) | | |
|---|---|---|
| Bacterial name | Strain No. | Culturing medium |
| *Acinetobacter baumannii* | ATCC 17978 | a |
| *Acinetobacter baumannii* | ATCC 19606 | a |
| *Acinetobacter baumannii* | ARLG-1791 | a |
| *Acinetobacter baumannii* | ARLG-1809 | a |
| *Acinetobacter baumannii* | ARLG-1852 | a |
| *Acinetobacter baumannii* | ARLG-1853 | a |
| *Acinetobacter baumannii* | ARLG-1881 | a |
| *Acinetobacter baumannii* | ATCC-BAA-1605 | a |
| *Acinetobacter baumannii* | ATCC-BAA-1789 | a |
| *Acinetobacter baumannii* | ATCC-BAA-1790 | a |

TABLE 6-continued

| Test Strains (20 Total Strains) | | |
|---|---|---|
| Bacterial name | Strain No. | Culturing medium |
| *Acinetobacter baumannii* | ATCC-BAA-1791 | a |
| *Acinetobacter baumannii* | ATCC-BAA-1792 | a |
| *Acinetobacter baumannii* | ATCC-BAA-1793 | a |
| *Acinetobacter baumannii* | ATCC-BAA-1794 | a |
| *Acinetobacter baumannii* | ATCC-BAA-1795 | a |
| *Acinetobacter baumannii* | ATCC-BAA-1796 | a |
| *Acinetobacter baumannii* | ATCC-BAA-1797 | a |
| *Acinetobacter baumannii* | ATCC-BAA-1798 | a |
| *Acinetobacter baumannii* | ATCC-BAA-1799 | a |
| *Acinetobacter baumannii* | ATCC-BAA-1800 | a |

Medium: a = CAMHB (cation adjusted Mueller-Hinton medium).

3. Experimental Steps 3.1 The compounds were diluted with DMSO up to 100 times of the highest concentration tested.

3.2 The compounds were diluted in gradient using the Echo555 pipette or manually diluted in a 2-fold gradient, depending on the compound's solubility. The steps of manual dilution are as follows (example): firstly, the compound or antibiotic was diluted to 100 times of the maximum final concentration tested, then 60 μL of compound mother liquor was added to the first column of the 96-well plate, and 30 μL of DMSO was added to each well in the second to the 12th column; 30 μL of the liquid was transferred from the first column to the second column. After being pipetted up and down to even, 30 μL was transferred to the third column, and was diluted in sequence at a 2-fold gradient for a total of 10 times; then 30 μL was removed from each well in the $11^{th}$ column, then a compound solution diluted at 2-fold gradient was obtained and 1 μL was transferred to a 96-well test plate.

3.3 Preparation of Strain Inoculums:

Aerobic bacteria: the strains were inoculated on MHA one day in advance and incubated overnight at 37° C. On the day of the assay, 5-6 single colonies were picked and suspended evenly in saline, and the bacterial concentration was adjusted to the turbidity of 0.5 McFarland standard (concentration is about $1\times10^8$ CFU/mL). The bacterial suspension was diluted at 200-fold with the corresponding liquid culture medium (Table 1), i.e., the bacterial concentration was ~$5\times10^5$ CFU/ml, and then 100 μL of the liquid was transferred to a 96-well round bottom plate (the 96-well plate with compound prepared in 4.2, Echo method) to obtain the test plate. If the compound was manually diluted, then 99 μL of the solution was transferred into a 96-well round bottom plate. The 96-well round bottom plate obtained above was placed into an incubator at 37° C. and 85% humidity to incubate for 20 h.

3.4 Determination of MIC: the lowest concentration of the compound at which the bacterial growth is completely or significantly inhibited by visual inspection will be defined as the MIC of the compound.

Table 7 shows the MIC of the antibacterial effect of the pharmaceutical composition of sulbactam sodium and avibactam sodium against 20 clinical strains of *Acinetobacter*

*baumannii*. Table 8 shows the MIC of the pharmaceutical composition combined at each ratio. The results showed that when the mass ratio of sulbactam sodium to avibactam sodium was 4:1, the MIC was lower than that when sulbactam sodium or avibactam sodium were administered alone, and was also lower than that when the mass ratio of sulbactam sodium to avibactam sodium was 2:1. The results showed that the antibacterial effect of sulbactam sodium and avibactam sodium was superior when they were administered at the mass ratio of 4:1 than that of sulbactam sodium or avibactam sodium when administered alone, and the antibacterial effect was also superior than that of sulbactam sodium and avibactam sodium administered at the mass ratio of 2:1. The results of MIC data indicated that when the sulbactam sodium and avibactam sodium were administered at a mass ratio of 4:1, the $MIC_{90}$ of sulbactam was 16 μg/mL and the $MIC_{90}$ of avibactam was 4 μg/mL, which could effectively reduce the administration dosage of sulbactam sodium and avibactam sodium to about ¼.

TABLE 7

Minimum Inhibitory Concentration of the Pharmaceutical Composition of Sulbactam Sodium and Avibactam Sodium against the Clinical Strains of *Acinetobacter baumannii*

| | MIC (μg/mL) | | | |
|---|---|---|---|---|
| Strains | Sulbactam sodium | Avibactam sodium | Sulbactam/Avibactam = 2/1 | Sulbactam/Avibactam = 4/1 |
| ATCC 17978 | 8 | >128 | 6 | 5 |
| ATCC 19606 | 2 | >128 | 3 | 2.5 |
| ARLG-1791 | 32 | >128 | 12 | 10 |
| ARLG-1809 | 32 | >128 | 24 | 20 |
| ARLG-1852 | 16 | >128 | 12 | 10 |
| ARLG-1853 | 32 | >128 | 24 | 20 |
| ARLG-1881 | 128 | >128 | 24 | 40 |
| ATCC-BAA-1605 | 32 | >128 | 12 | 20 |
| ATCC-BAA-1789 | 4 | >128 | 6 | 5 |
| ATCC-BAA-1790 | 16 | >128 | 12 | 20 |
| ATCC-BAA-1791 | 8 | >128 | 6 | 10 |
| ATCC-BAA-1792 | 32 | >128 | 12 | 10 |
| ATCC-BAA-1793 | 32 | >128 | 24 | 20 |
| ATCC-BAA-1794 | 8 | >128 | 6 | 10 |
| ATCC-BAA-1795 | 64 | >128 | 12 | 10 |
| ATCC-BAA-1796 | 16 | >128 | 12 | 10 |
| ATCC-BAA-1797 | 8 | >128 | 12 | 10 |
| ATCC-BAA-1798 | 16 | >128 | 24 | 20 |
| ATCC-BAA-1799 | 64 | >128 | 24 | 20 |
| ATCC-BAA-1800 | 32 | >128 | 24 | 20 |

TABLE 8

Results of Minimum Inhibitory Concentrations

| Drug (Combination) | MIC range (μg/mL) | $MIC_{50}$ (μg/mL) | $MIC_{90}$ (μg/mL) |
|---|---|---|---|
| Sulbactam sodium | 2-128 | 32 | 64 |
| Avibactam sodium | >128 | >128 | >128 |
| Sulbactam sodium/avibactam sodium = 2:1 | 3-24 | 12 | 24 |
| Sulbactam sodium/avibactam sodium = 4:1 | 2.5-40 | 10 | 20 |

Example 3: Pharmacokinetics of Sulbactam Sodium and Avibactam Sodium in Plasma and Bronchoalveolar Lavage Fluid of Female CD-1 Mice This example evaluated the pharmacokinetic profile of sulbactam sodium and avibactam in the plasma and bronchoalveolar lavage fluid of female CD-1 mice. The method is as follows: female CD-1 mice weighing 25-33 g were selected and divided into different groups, with 3 mice in each group, and sulbactam at dose of 150 mg/kg and avibactam at dose of 150 mg/kg were intravenously administered to the mice. An appropriate amount of the test drug was accurately weighed and mixed with the appropriate volume of vehicle (5% DMSO+0.5% Tween 80 in normal saline) to obtain a clear solution for the test in Table 9. The formulation solution for injection was prepared to sterile filtration through a 0.22 μm filter prior to administration. The mice were dosed with the drug within 30 min after the formulated solution for injection was prepared. A 1.5 mL of the formulation solution for injection was transferred into a polypropylene microcentrifuge tube for dose verification by LC/UV or LC-MS/MS.

Sample collection (Table 10, M01 to M12 indicate the mouse codes): approximately 50 μL of blood was collected from the saphenous vein or other suitable sites of each animal into polypropylene tubes at 0.25 h, 1 h, 4 h, and 6 h post-dose. All blood samples were transferred to pre-frozen EDTA-$K_2$ tubes and placed on wet ice until centrifugation. Approximately 200 μL of blood was collected from the saphenous vein or other suitable sites of each animal into polypropylene tubes at 0.5 h, 3 h, 5 h, and 8 h post-dose (terminal time points).

Plasma: approximately 100 μL of blood sample was transferred into pre-cooled commercial EDTA-$K_2$ tubes and placed on wet ice until centrifugation. After the blood samples were centrifuged at approximately 4° C. and 3, 200 g for 10 min, plasma was collected and transferred to pre-labeled 96-well plates or polypropylene tubes, flash frozen on dry ice, and stored at ≤−60° C. until the analysis by LC-MS/MS.

Serum: approximately 100 μL of blood sample was transferred into a tube without anticoagulant and placed on wet ice for approximately 30 min and centrifuged at 4° C. and 3,000 g for 10 min, and the serum was collected and transferred into pre-labeled PP tubes placed on wet ice. After the completion of all the collections, serum samples were stored at −60° C. until being sent to the animal experimental team to determine urea concentration.

Bronchoalveolar lavage fluid (BALF): pre-cooled tracheo-alveolar lavage fluid was injected into the trachea or predefined bronchi. After a full expansion of the lung tissue, the lavage fluid was slowly drawn out with a syringe 30 s later. The lung was lavaged three times. During the last lavage, the lung tissue was gently squeezed to restore the fluid. To prevent contamination of other lung tissues, the corresponding bronchi were ligated. Both lungs of the mice were perfused with 0.8 mL.

Approximately 800 uL of BALF was collected at 0.5 h, 3 h, 5 h and 8 h (terminal time point). Approximately 200 μL of the BALF samples were transferred into a polypropylene tube, rapidly frozen on dry ice, maintained at ≤−60° C., and sent to the animal experimental team to determine urea concentration. The remaining BALF samples (approximately 600 μL) were rapidly frozen on dry ice and maintained at ≤−60° C. until being submitted for drug concentration analysis by LC-MS/MS.

TABLE 9

| Pharmacokinetic Study Design | | | | | | | | |
|---|---|---|---|---|---|---|---|---|
| Group No. | Tested sample | Number of animals | Sex | Mode of administration | Dose administered (mg/kg) | Dosing concentration (mg/mL) | Dosing volume (mL/kg) | Vehicle |
| 01 | Sulbactam sodium, avibactam | 3 | Female | Intravenous dripping | 25 | 10 | 2.5 | 5% DMSO + 0.5% tween 80 in saline |
| 02 | Sulbactam sodium, avibactam | 3 | Female | Intravenous dripping | 150 | 10 | 15 | |
| 03 | Sulbactam sodium, avibactam | 3 | Female | Intravenous dripping | 150 | 10 | 15 | |
| 04 | Sulbactam sodium, avibactam | 3 | Female | Intravenous dripping | 150 | 10 | 15 | |

TABLE 10

| Sample Collection | | | | | | |
|---|---|---|---|---|---|---|
| Group | Analyte | Dose administered (mg/kg) | Sampling time point (h) | BALF | Plasma | Serum |
| 01 | Sulbactam sodium, | 25 | 0.25 | | 1 | |
| | avibactam Sodium | | 0.5 | | 1 | |
| | Sulbactam sodium, avibactam sodium, urea | | 0.5 | 1 | | |
| | Urea | | 0.5 | | | 1 |
| 02 | Sulbactam sodium, | 150 | 1 | | 1 | |
| | avibactam Sodium | | 3 | | 1 | |
| | Sulbactam sodium, avibactam sodium, urea | | 3 | 1 | | |
| | Urea | | 3 | | | 1 |
| 03 | Sulbactam sodium, | 150 | 4 | | 1 | |
| | avibactam Sodium | | 5 | | 1 | |
| | Sulbactam sodium, avibactam sodium, urea | | 5 | 1 | | |
| | Urea | | 5 | | | 1 |
| 04 | Sulbactam sodium, | 150 | 6 | | 1 | |
| | avibactam Sodium | | 8 | | 1 | |
| | Sulbactam sodium, avibactam sodium, urea | | 8 | 1 | | |
| | Urea | | 8 | | | 1 |

The results are shown in Tables 11-13. The results showed that the plasma concentrations of both sulbactam sodium and avibactam sodium were maintained at above 8 g/mL and 2 μg/mL (i.e., the MIC of this strain BAA-1795) for more than 50% of the dosing interval at doses of 75 mg/kg and 18.75 mg/kg, see Tables 11, 12 and 13.

TABLE 11

| Pharmacokinetic Parameters | | | | |
|---|---|---|---|---|
| | avibactam sodium | | sulbactam sodium | |
| PK parameters | Mean plasma concentration | Mean BALF concentration | Mean plasma concentration | Mean BALF concentration |
| $C_{max}$ (ng/mL) | 18845 | 626 | 19645 | 617 |
| $T_{max}$ (h) | 1.00 | 3.00 | 1.00 | 3.00 |
| $T_{1/2}$ (h) | 1.23 | 0.762 | 0.874 | 0.725 |
| $Vd_{ss}$ (L/kg) | 1.31 | — | 1.26 | — |
| Cl (mL/min/kg) | 48.7 | — | 47.2 | — |
| $AUC_{0\text{-}last}$ (ng · h/mL) | 51289 | 1319 | 52886 | 1313 |
| $MRT_{0\text{-}last}$ (h) | 0.439 | 1.71 | 0.440 | 1.72 |
| $^{a}$AUC Ratio | — | 0.0257 | — | 0.0248 |

TABLE 12

| Concentrations of Avibactam | | | | |
|---|---|---|---|---|
| Time (h) | Plasma concentration (ng/mL) Mean + SD | BALF concentration (ng/mL) Mean + SD | ELF concentration (ng/mL) Mean + SD | BALF/plasma ratio Mean |
| 0.25 | 16497 ± 2257 | ND | ND | ND |
| 0.50 | 17919 ± 2038 | 849 ± 210 | 5395 ± 2386 | 0.0474 |
| 1.00 | 18845 ± 3069 | ND | ND | ND |
| 3.00 | 18328 ± 4531 | 626 ± 459 | 4729 ± 2414 | 0.0319 |
| 4.00 | 285 ± 226 | ND | ND | ND |
| 5.00 | 123 ± 34.8 | 19.0 ± 11.6 | 129 ± 75.2 | 0.153 |
| 6.00 | 57.8 ± 3.10 | ND | ND | ND |
| 8.00 | 28.5 ± 9.52 | 5.37 ± ND | 22.2 ± ND | 0.211 |

TABLE 13

| Concentrations of Sulbactam | | | | |
|---|---|---|---|---|
| Time (h) | Plasma concentration (ng/mL) Mean ± SD | BALF concentration (ng/mL) Mean ±SD | ELF concentration (ng/mL) Mean ± SD | BALF/ plasma ratio Mean |
| 0.25 | 16172 ± 1472 | ND | ND | ND |
| 0.50 | 17474 ± 1998 | 892 ± 116 | 5584 ± 2061 | 0.0512 |
| 1.00 | 19645 ± 4251 | ND | ND | ND |
| 3.00 | 18306 ± 4385 | 617 ± 460 | 4652 ± 2417 | 0.0315 |
| 4.00 | 406 ± 246 | ND | ND | ND |
| 5.00 | 197 ± 120 | 21.7 ± 8.03 | 149 ± 20.9 | 0.173 |
| 6.00 | 31.3 ± 9.63 | ND | ND | ND |
| 8.00 | 19.4 ± 10.1 | 4.3 ± ND | 18.6 ± ND | 0.380 |

Example 4: Pharmacodynamics of Sulbactam Sodium and Avibactam Sodium in Animal Model of Lung Infection This example evaluated the therapeutic effect of sulbactam sodium and avibactam in female CD-1 mice. Female CD-1 mice weighing 27 g-29 g were selected for the study, and each mouse was inoculated with *Acinetobacter baumannii* ATCC BAA-1795 strain at a dose of 1.60 E+07 CFU/mouse. The 5 mice in each group were dosed with sulbactam sodium/avibactam at doses of 300 mg/kg/75 mg/kg, 150 mg/kg/37.5 mg/kg and 75 mg/kg/18.75 mg/kg via intravenous injection, once every 6 h with administration for 3 h each time. Tigecycline was used as the positive control drug and was intravenously administered at 300 mg/kg twice daily. The 0-h control group was used to detect the inoculum size of the strain, and the 24-h control group was used to detect the colonized quantity of the strain. At 24 h after infection, the mice were euthanized via carbon dioxide inhalation. The lungs of the mice were collected aseptically into 15 mL centrifuge tubes each containing 5 mL of sterile normal saline, then the lung tissue was ground by a tissue homogenizer to obtain the lung tissue homogenate liquid. A 200 μL of each homogenate sample was taken and diluted 10 times in a 96-well plate (with the dilution system consisting of 20 μL of bacterial liquid and 180 μL of normal saline) to obtain a total of 6 dilution gradients from 100 to 10-5. Then, 10 μL of bacterial liquid at each dilution gradient was taken and placed on a TSA plate. After overnight incubation at 37° C. in an incubator, the number of CFUs at each dilution gradient was counted, and the bacterial load (CFU/lung) in the corresponding lung tissue was calculated based on the corresponding dilution fold. The results are shown in the FIGURE.

The FIGURE shows that the three different doses (i.e., 300 mg/kg/75 mg/kg, 150 mg/kg/37.5 mg/kg and 75 mg/kg/18.75 mg/kg) of sulbactam and avibactam (4:1) achieved good antibacterial effect and no significant difference between different doses, which indicated that the plasma concentrations of both sulbactam and avibactam were maintained at above 8 μg/mL and 2 μg/mL (i.e., the MIC of the strain BAA-1795) for more than 50% of the dosing interval after repeated administration at the doses of 75 mg/kg and 18.75 mg/kg. The results also verified the PK-PD relationship that could realize better bacteriostatic effect when the plasma concentration was maintained above the MIC for more than 50% of the dosing interval.

Example 5: Effective Doses of Sulbactam Sodium and Avibactam Sodium in Humans Based on the MIC results obtained from Examples 1 and 2, when sulbactam sodium: avibactam sodium=4:1, the $MIC_{90}$ of sulbactam against the test bacteria was 16 μg/mL and the $MIC_{50}$ was 8 μg/mL; and the $MIC_{90}$ of avibactam against the test bacteria was 4 μg/mL and the $MIC_{50}$ was 2 μg/mL. Example 4 confirmed that the free plasma concentrations of both sulbactam sodium and avibactam sodium were maintained more than 50% of the dosing interval at above 8 and 2 μg/mL (i.e., the MIC of the strain BAA-1795) after repeated administration at the doses of 75 mg/kg and 18.75 mg/kg.

For β-lactam antibacterial drugs, good antibacterial effect can be achieved when the blood concentration is maintained above the MIC for more than 40% of the dosing interval (Pharmacodynamic/Pharmacodynamic Parameters: Rationale for Antibacterial Dosing in Mice and Men).

The protein binding of sulbactam and avibactam is approximately 5.2% and 8%. For sulbactam or a pharmaceutically acceptable salt thereof, the plasma concentrations for the administration at a dose of 2 g, q8 h via infusion for 3 h could maintain 44% of the dosing interval at above 2 μg/mL. The administration at a dose of 2 g, q8 h via infusion for 3 h could maintain the plasma concentrations at above 4 μg/mL for 19% of the dosing interval (Pharmacodynamics Modeling to Optimize Dosing Regimens of Sulbactam, Table 2 and FIG. 1B). For avibactam or a pharmaceutically acceptable salt thereof, the plasma concentrations for the administration at a dose of 0.5 g, q8 h via infusion for 2 h could maintain 30% or 50% of the dosing interval at above 8 or 4 μg/mL (Pharmacokinetic-Pharmacodynamic Target Attention Analyses to Determine Optimal Dosing of Ceftazidime-Avibactam for the Treatment of Acute Pulmonary Exacerbations in Patients with Cystic Fibrosis, FIG. 2).

Therefore, it can be concluded that when sulbactam sodium is administered at a dose of 2 g, q6 h via infusion for 3 h, the mean plasma concentrations could be maintained at 32 μg/mL or above within approximately more than 40% of the dosing interval. When avibactam sodium is administered via intravenous dripping for 3 h at a dose of 0.5 g, q6 h, the mean plasma concentrations could be maintained at 8 or 4 μg/mL or above within approximately more than 40% or 60% of the dosing interval.

Example 6: Detection of Stability of pH Values of the Mixture of Sulbactam Sodium and Avibactam Sodium In this example, the purity of sulbactam sodium and avibactam sodium in the mixture stored in different pH buffer solutions at 20° C. for 24 h (the purity was calculated as 100% at 0 h) were tested when the two drugs were mixed at the mass ratio of 4:1 (sulbactam sodium 1 mg/mL; avibactam sodium 0.25 mg/mL).

Chromatographic conditions for the stability study of the mixture of sulbactam and avibactam at different pH values:

Instruments: Agilent 1100 high-performance liquid chromatography, DAD detector; column: Waters XTerra RP18, 5 μm×4.6 mm×250 mm, PN: 186000496; flow rate: 1.0 mL/min; column temperature: 40° C.; injection volume: 10 μL; injection concentration: sulbactam sodium at 1 mg/mL, avibactam sodium at 0.25 mg/mL; detection wavelength: 215 nm; the temperature of sample tray: 20° C.; mobile phase A: 0.544 g/L potassium dihydrogen phosphate (can be adjusted to pH 4.00 if necessary); mobile phase B: acetonitrile; gradient run and data acquisition time: 25 min.

Elution Gradient:

| Time (min) | Mobile phase A, % | Mobile phase B, % |
|---|---|---|
| 0 | 98 | 2 |
| 7.5 | 50 | 50 |
| 8.5 | 50 | 50 |
| 9 | 98 | 2 |
| 13 | 98 | 2 |
| 25 | 98 | 2 |

TABLE 14

Purity of Avibactam and Sulbactam in Different pH Buffers

| | Avibactam (monomer) | Sulbactam (monomer) | Avibactam (in mixture) | Sulbactam (in mixture) |
|---|---|---|---|---|
| pH 4.0 buffer: | −24.20% | −0.27% | −23.74% | −0.57% |
| pH 4.5 buffer: | −2.31% | −0.45% | −1.42% | 0.11% |
| pH 5.0 buffer: | −0.71% | −0.29% | −0.99% | −0.42% |
| pH 5.5 buffer: | −0.77% | −1.52% | −0.54% | −0.70% |
| pH 6.0 buffer: | −1.75% | −0.40% | −1.76% | −0.29% |
| pH 7.3 buffer: | −0.81% | 0.28% | −1.06% | −0.15% |
| pH 8.0 buffer: | −8.87% | −5.70% | −8.81% | −5.53% |

As shown in Table 14, there were minimal changes in the purity of avibactam and sulbactam in the mixture within the pH range of 5-7.3, which indicated the mixture is stable over this range of pH values.

The foregoing descriptions of the embodiment provided by explanations and illustrations do not limit the scope defined by the appended claims. The multiple variations of the embodiment currently presented in the present application are readily apparent to those of ordinary skilled in the art and maintained within the scope as defined by the appended claims and their equivalent embodiment methods.

What is claimed is:

1. A pharmaceutical composition comprising sulbactam or a pharmaceutically acceptable salt thereof and avibactam or a pharmaceutically acceptable salt thereof, and optionally a pharmaceutically acceptable carrier, wherein unit dose ratio of said sulbactam or the pharmaceutically acceptable salt thereof to said avibactam or the pharmaceutically acceptable salt thereof is about 8:1 to about 4:1, unit dose of said sulbactam or the pharmaceutically acceptable salt thereof is about 1 g-4 g, and unit dose of said avibactam or the pharmaceutically acceptable salt thereof is about 0.125 g-1 g.

2. The pharmaceutical composition of claim 1, wherein the unit dose of said sulbactam or the pharmaceutically acceptable salt thereof is about 2 g.

3. The pharmaceutical composition of claim 1, wherein the unit dose of said avibactam or the pharmaceutically acceptable salt thereof is about 1 g.

4. The pharmaceutical composition of claim 1, wherein the unit dose of said avibactam or the pharmaceutically acceptable salt thereof is about 0.5 g.

5. The pharmaceutical composition of claim 1, which has a pH value of about 5 to about 7.3.

6. A kit or an administration device, which comprises the pharmaceutical composition of claim 1.

7. A method for preventing, treating and/or alleviating bacterial infections, wherein said method comprises administering to a patient in need thereof sulbactam or a pharmaceutically acceptable salt thereof and avibactam or a pharmaceutically acceptable salt thereof, ratio of administration dosage of said sulbactam or the pharmaceutically acceptable salt thereof to said avibactam or the pharmaceutically acceptable salt thereof is about 8:1 to about 4:1 and the administration dosage of said sulbactam or the pharmaceutically acceptable salt thereof is about 4 g-12 g/day, and the administration dosage of said avibactam or the pharmaceutically acceptable salt thereof is about 0.5 g-3 g/day.

8. The method of claim 7, wherein dosing interval of said sulbactam or the pharmaceutically acceptable salt thereof is every 6 hours-8 hours.

9. The method of claim 7, wherein dosing frequency of said sulbactam or the pharmaceutically acceptable salt thereof is 2 times-4 times daily.

10. The method of claim 9, wherein the administration dosage of said sulbactam or the pharmaceutically acceptable salt thereof is 2 g each time.

11. The method of claim 7, wherein dosing interval of said avibactam or the pharmaceutically acceptable salt thereof is every 6 hours-8 hours.

12. The method of claim 7, wherein dosing frequency of said avibactam or the pharmaceutically acceptable salt thereof is 2 times-4 times daily.

13. The method of claim 12, wherein the administration dosage of said avibactam or the pharmaceutically acceptable salt thereof is 0.5 g each time.

14. The method of claim 7, which comprises intravenous injection.

15. The method of claim 7, wherein bacteria are resistant to one or more β-lactam antibiotics.

16. The method of claim 7, wherein bacteria comprise *Acinetobacter baumannii*.

17. The method of claim 7, which is used in combination with polymyxin.

18. The method of claim 7, which is used in combination with tigecycline.

* * * * *